United States Patent [19]
Acklin et al.

[11] Patent Number: 6,117,873
[45] Date of Patent: Sep. 12, 2000

[54] SUBSTITUTED AMINOALKANE PHOSPHONIC ACIDS

[75] Inventors: Pierre Acklin, Basel, Switzerland; Hans Allgeier, Lörrach, Germany; Yves Auberson, Allschwil; Silvio Ofner, Münchenstein, both of Switzerland; Siem Jacob Veenstra, Lörrach, Germany

[73] Assignee: Novartis AG, Basel, Switzerland

[21] Appl. No.: 09/297,010

[22] PCT Filed: Oct. 22, 1997

[86] PCT No.: PCT/EP97/05843

§ 371 Date: Apr. 23, 1999

§ 102(e) Date: Apr. 23, 1999

[87] PCT Pub. No.: WO98/17672

PCT Pub. Date: Apr. 30, 1998

[30] Foreign Application Priority Data

Oct. 24, 1996 [CH] Switzerland ............... 2621/96

[51] Int. Cl.⁷ ............... A61K 31/495; C07F 9/02
[52] U.S. Cl. ............... 514/249; 544/337
[58] Field of Search ............... 544/337; 514/249

[56] References Cited

U.S. PATENT DOCUMENTS

| | | | |
|---|---|---|---|
| 4,948,794 | 8/1990 | Honore et al. | 514/249 |
| 5,118,675 | 6/1992 | Jirkovsky et al. | 514/80 |
| 5,166,155 | 11/1992 | Jorgensen et al. | 514/249 |
| 5,283,244 | 2/1994 | Sakamoto et al. | 514/249 |
| 5,480,883 | 1/1996 | Spada et al. | 514/249 |
| 5,514,680 | 5/1996 | Weber et al. | 514/249 |

FOREIGN PATENT DOCUMENTS

| | | |
|---|---|---|
| 2161425 | 11/1994 | Canada . |
| WO 94 25469 | 11/1994 | WIPO . |
| WO 97 03079 | 1/1997 | WIPO . |
| WO 97 08155 | 3/1997 | WIPO . |

Primary Examiner—Deborah C. Lambkin
Attorney, Agent, or Firm—Joseph J. Borovian

[57] ABSTRACT

Compounds of the formula I

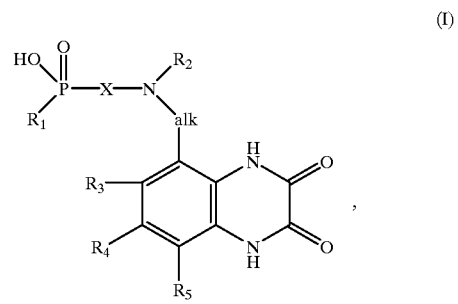

in which $R_1$ is hydroxyl or an aliphatic, araliphatic or aromatic radical, X is a divalent aliphatic, cycloaliphatic, cycloaliphatic-aliphatic, araliphatic, heteroarylaliphatic or aromatic radical, $R_2$ is hydrogen or an aliphatic or araliphatic radical, alk is lower alkylidene and $R_3$, $R_4$ and $R_5$ independently of one another are hydrogen, lower alkyl, halogen, trifluoromethyl, cyano or nitro, and their salts can be used for the treatment of pathological conditions which respond to blockage of excitatory amino acid receptors, and for the production of pharmaceutical preparations.

9 Claims, No Drawings

SUBSTITUTED AMINOALKANE PHOSPHONIC ACIDS

This application is a 371 of PCT/EP97/05843 Oct. 22, 1997.

The invention relates to compounds of the formula I

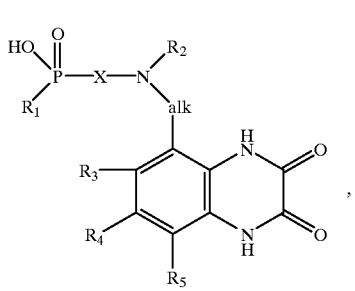

(I)

in which
- $R_1$ is hydroxyl or an aliphatic, araliphatic or aromatic radical,
- X is a divalent aliphatic, cycloaliphatic, cycloaliphatic-aliphatic, araliphatic, heteroarylaliphatic or aromatic radical,
- $R_2$ is hydrogen or an aliphatic or araliphatic radical, alk is lower alkylidene and
- $R_3$, $R_4$ and $R_5$ independently of one another are hydrogen, lower alkyl, halogen, trifluoromethyl, cyano or nitro, and their salts, processes for their preparation and pharmaceutical preparations comprising them.

Novel compounds of the formula I are, for example, those in which a1) $R_4$ is other than nitro when X is methylene, 3-hydroxybenzylidene, 3-methoxybenzylidene, 3-pyridylmethylene, ethylene, oxoethylene, ethylidene, 1,3-propylene, 1,3-(1-carboxy)propylene, cyclopropylene or 1,4-butylene, $R_1$ is hydroxyl, alk is methylene and $R_2$, $R_3$ and $R_5$ are hydrogen, or when X is methylene, $R_1$ is methyl or benzyl, alk is methylene and $R_2$, $R_3$ and $R_5$ are hydrogen, or when X is butylene, $R_1$ is hydroxyl, alk is methylene, $R_2$ is methyl and $R_3$ and $R_5$ are hydrogen and b1) $R_4$ is other than bromine when X is methylene or ethylidene, $R_1$ is hydroxyl, alk is methylene and $R_2$, $R_3$ and $R_5$ are hydrogen, or, for example, those in which a2) X is other than methylene, 3-hydroxybenzylidene, 3-methoxybenzylidene, 3-pyridylmethylene, ethylene, oxoethylene, ethylidene, 1,3-propylene, 1,3-(1-carboxy)propylene, cyclopropylene and 1,4-butylene when $R_1$ is hydroxyl and $R_2$ is hydrogen, b2) X is other than 1,4-butylene when $R_1$ is hydroxyl and $R_2$ is methyl, and c) X is other than methylene when $R_1$ is methyl or benzyl.

Aliphatic radicals are, for example, lower alkyl, lower alkenyl or lower alkanoyl radicals.

Araliphatic radicals are, for example, phenyl-lower alkyl or naphthyl-lower alkyl radicals.

Aromatic radicals are, for example, phenyl or naphthyl radicals.

Divalent aliphatic radicals are, for example, lower alkylene, oxo-lower alkylene, oxo-lower alkenylene, lower alkylidene, polyhalo-lower alkylidene, carboxy-lower alkylidene, hydroxy-lower alkylidene, lower alkoxy-lower alkylidene or lower alkylthio-lower alkylidene.

Divalent cycloaliphatic radicals are, for example, unfused or benzo-fused cycloalkylene, cycloalkylidene or cycloalkenylidene radicals, such as 3- to 6-membered cycloalkylene, 3- to 6-membered cycloalkylidene or 3- to 6-membered benzocycloalkenylidene.

Divalent cycloaliphatic-aliphatic radicals are, for example, 3- to 6-membered cycloalkyl-lower alkylene or cycloalkyl-lower alkylidene radicals.

Divalent araliphatic radicals are, for example, phenyl-lower alkylene, phenyl(oxo)-lower alkylene or phenyl-lower alkylidene radicals.

Divalent heteroaryl aliphatic radicals are, for example, pyrrolyl-lower alkylidene, furyl-lower alkylidene, thienyl-lower alkylidene or pyridyl-lower alkylidene radicals.

Divalent aromatic radicals are, for example, phenylene or naphthylene radicals.

Aliphatic radicals are, for example, lower alkyl or lower alkenyl radicals.

Araliphatic radicals are, for example, phenyl-lower alkyl or naphthyl-lower alkyl radicals.

Aromatic radicals are, for example, phenyl or naphthyl radicals.

The ring system of the cycloalkylene, cycloalkylidene, unfused or benzo-fused cycloalkylene, cycloalkylidene or cycloalkenylidene, cycloalkyl-lower alkylidene, cycloalkenyl-lower alkylidene, phenyl-lower alkylene, phenyl(oxo)-lower alkylene, phenyl-lower alkylidene, furyl-lower alkylidene, thienyl-lower alkylidene, pyridyl-lower alkylidene, phenylene, naphthylene, phenyl-lower alkyl and naphthyl-lower alkyl radicals mentioned can be unsubstituted or substituted, such as mono-, di- or trisubstituted, in a customary manner, for example by lower alkyl, lower alkoxy, phenoxy, hydroxyl, halogen, trifluoromethyl, di-lower alkylamino, lower alkanoylamino, nitro, carboxyl, lower alkoxycarbonyl, carbamoyl and/or cyano.

3- to 6-membered benzocycloalkenylidene is, for example, indanylidene or tetrahydronaphthylidene, such as indan-2,2-ylidene.

3- to 6-membered cycloalkylene is, for example, cyclopropylene, 1,2-cyclobutylene, 1,2-cyclopentylene or 1,2-cyclohexylene.

3- to 6-membered cycloalkylidene is, for example, cyclopropylidene, cyclobutylidene, cyclopentylidene or cyclohexylidene.

3- to 6-membered cycloalkyl-lower alkylene is, for example, 3- to 6-membered cycloalkyl-$C_1$–$C_4$alkylene, in which cycloalkyl is, for example, cyclopropyl, cyclobutyl, cyclopentyl or cyclohexyl.

3- to 6-membered cycloalkyl-lower alkylidene is, for example, 3- to 6-membered cycloalkyl-$C_1$–$C_4$alkylidene, in which cycloalkyl is, for example, cyclopropyl, cyclobutyl, cyclopentyl or cyclohexyl.

Above and below, lower radicals and compounds are understood as meaning, for example, those which have up to and including 7, preferably up to and including 4, carbon atoms (C atoms).

Carboxy-lower alkylidene is, for example, carboxy-$C_1$–$C_4$alkylidene, such as carboxymethylene, furthermore 2-carboxyethylidene, 3-carboxypropylidene or 4-carboxybutylidene.

Di-lower alkylamino is, for example, di-$C_1$–$C_4$alkylamino, such as dimethylamino, diethylamino, N-ethyl-N-methylamino, N-propyl-N-methylamino, N-isopropyl-N-methylamino or N-butyl-N-methylamino.

Furyl-lower alkylidene is, for example, furyl-$C_1$–$C_4$alkylidene, such as furylmethylene, furthermore 2-furylethylidene, 3-furylpropylidene or 4-furylbutylidene.

Halogen is, for example, halogen of atomic number up to and including 35, such as fluorine, chlorine or bromine.

Hydroxy-lower alkylidene is, for example, hydroxy-$C_2$–$C_7$alkylidene, in particular hydroxy-$C_2$–$C_4$alkylidene, such as 2-hydroxyethylidene, 3-hydroxypropylidene or 4-hydroxybutylidene.

Naphthyl-lower alkyl is, for example, naphthyl-$C_1$–$C_4$alkyl which is unsubstituted or substituted as indicated, such as naphthylmethyl, 2-naphthylethyl, 3-naphthylpropyl or 4-naphthylbutyl.

Lower alkanoylamino is, for example, $C_1$–$C_7$alkanoylamino, such as acetylamino, propionylamino, butyrylamino, isobutyrylamino or pivaloylamino.

Lower alkenyl is, for example, $C_2$–$C_7$alkenyl, preferably $C_3$–$C_4$alkenyl, such as allyl or but-2-enyl.

Lower alkoxy is, for example, $C_1$–$C_7$alkoxy, preferably $C_1$–$C_5$alkoxy, such as methoxy, ethoxy, propoxy, isopropoxy, butoxy, isobutoxy, secondary butoxy, tertiary butoxy, pentoxy or a hexyloxy or heptyloxy group.

Lower alkoxycarbonyl is, for example, $C_1$–$C_7$alkoxycarbonyl, preferably $C_1$–$C_4$alkoxycarbonyl, such as methoxycarbonyl, ethoxycarbonyl, propoxycarbonyl, isopropoxycarbonyl or butoxycarbonyl, but can also be isobutoxycarbonyl, secondary butoxycarbonyl, tert-butoxycarbonyl or a pentoxycarbonyl, hexyloxycarbonyl or heptyloxycarbonyl group.

Lower alkoxy-lower alkylidene is, for example, $C_1$–$C_4$alkoxy-$C_1$–$C_4$alkylidene, such as 2-methoxyethylidene, ethoxymethylene, 2-methoxyethylidene, 2-ethoxyethylidene, 3-methoxypropylidene or 4-methoxybutylidene.

Lower alkyl is, for example, $C_1$–$C_7$alkyl, preferably $C_1$–$C_4$alkyl, such as, in particular, methyl or secondarily ethyl, propyl, isopropyl or butyl, but can also be isobutyl, secondary butyl, tertiary butyl or a $C_5$–$C_7$alkyl group, such as a pentyl, hexyl or heptyl group.

Lower alkylene can be straight-chain or branched and can be bonded in any desired position and is, for example, straight-chain or branched $C_1$–$C_4$alkylene, such as, in particular, methylene, furthermore 1,2-ethylene, 1,3- or 1,2-propylene or 1,4-, 1,3- or 2,3-butylene.

Lower alkylidene can be straight-chain or branched and can be geminally bonded in any desired position and is, for example, straight-chain or branched $C_1$–$C_4$alkylene, such as, in particular, methylene, 1,1-ethylidene, 1,1- or 2,2-propylidene or 1,1-butylidene.

Lower alkylthio-lower alkylidene is, for example, $C_1$–$C_4$alkylthio-$C_1$–$C_4$alkylidene, such as methylthiomethylene, ethylthiomethylene, 2-methylthioethylidene, 2-ethylthioethylidene, 3-methylthiopropylidene or 4-methylthiobutylidene.

Oxo-lower alkenylene is preferably bonded to the N atom marked in formula I via the C atom bearing the oxo group and is, for example, appropriate oxo-$C_3$–$C_4$alkenylene, such as, in particular, 1-oxoprop-2-enylene or 1-oxobut-2-enylene.

Oxo-lower alkylene is preferably bonded to the N atom marked in formula I via the C atom bearing the oxo group and is, for example, appropriate oxo-$C_2$–$C_4$alkylene, such as, in particular, 1-oxoethylene or 1-oxopropylene, furthermore 1-oxobutylene.

Phenyl(oxo)-lower alkylene is preferably bonded to the N atom marked in formula I via the C atom bearing the oxo group and is, for example, appropriate phenyl(oxo)-$C_2$–$C_4$alkylene, such as, in particular, 1-oxo-2-phenylethylene.

Phenyl-lower alkyl is, for example, phenyl-$C_1$–$C_4$alkyl which is unsubstituted or substituted as indicated, such as benzyl, 2-phenylethyl, 3-phenylpropyl or 4-phenylbutyl.

Phenyl-lower alkylene is, for example, phenyl-$C_2$–$C_4$alkylene which is unsubstituted or substituted as indicated, such as 2-phenylethylene, 3-phenylpropylene or 4-phenylbutylene.

Phenyl-lower alkylidene is, for example, phenyl-$C_1$–$C_4$alkylidene, such as benzylidene, furthermore 2-phenylethylidene, 3-phenylpropylidene or 4-phenylbutylidene.

Polyhalo-lower alkylidene is, for example, polyhalo-$C_1$–$C_4$alkylidene, such as, in particular, 2,2,2-trifluoroethylidene.

Pyridyl-lower alkylidene is, for example, pyridyl-$C_1$–$C_4$alkylidene, such as pyridylmethylene, furthermore 2-pyridylethylidene, 3-pyridylpropylidene or 4-pyridylbutylidene.

Pyrrolyl-lower alkylidene is, for example, pyrrolyl-$C_1$–$C_4$alkylidene, such as pyrrolylmethylene, furthermore 2-pyrrolylethylidene, 3-pyrrolyipropylidene or 4-pyrrolylbutylidene.

Thienyl-lower alkylidene is, for example, thienyl-$C_1$–$C_4$alkylidene, such as thienylmethylene, furthermore 2-thienylethylidene, 3-thienylpropylidene or 4-thienylbutylidene.

The compounds of the formula I can form salts with bases. Compounds of the formula I having basic groups can furthermore form acid addition salts and internal salts.

Salts of compounds of the formula I with bases are, for example, their salts with pharmaceutically acceptable bases, such as nontoxic metal salts derived from metals of Groups Ia, Ib, IIa and IIb, e.g. alkali metal salts, in particular sodium or potassium salts, alkaline earth metal salts, in particular calcium or magnesium salts, as well as ammonium salts with ammonia or organic amines or quaternary ammonium bases, such as free or C-hydroxylated aliphatic amines, in particular mono-, di- or tri-lower alkylamines, e.g. methyl-, ethyl- or diethylamine, mono-, di- or tri(hydroxy-lower alkyl) amines, such as ethanolamine, diethanolamine or triethanolamine, tris(hydroxymethyl)naphthyl radicals or 2-hydroxy-tertiary butylamine, or N-(hydroxy-lower alkyl)-N,N-di-lower alkylamines or N-(polyhydroxy-lower alkyl)-N-lower alkylamines, such as 2-(dimethylamino)ethanol or D-glucamine or choline, or quaternary aliphatic ammonium hydroxides, e.g. tetrabutylammonium hydroxide.

Acid addition salts of compounds of the formula I are, for example, their pharmaceutically acceptable salts with suitable mineral acids, such as hydrohalic acids, sulfuric acid or phosphoric acid, e.g. hydrochlorides, hydrobromides, sulfates, hydrogensulfates or phosphates, salts with suitable carboxylic acids, such as free or hydroxylated lower alkanoic acids, e.g. acetic acid, glycolic acid, propionic acid, lactic acid or pivalic acid, lower alkanedicarboxylic acids which are free or hydroxylated and/or substituted by oxo, e.g. oxalic acid, succinic acid, fumaric acid, maleic acid, tartaric acid, citric acid, pyruvic acid, malic acid, ascorbic acid, furthermore with aromatic, heteroaromatic or araliphatic carboxylic acids, such as benzoic acid, nicotinic acid or mandelic acid, and salts with suitable aliphatic or aromatic sulfonic acids or N-substituted sulfamic acids, e.g. methanesulfonates, benzenesulfonates, p-toluenesulfonates or N-cyclohexylsulfamates (cyclamates).

Both full and partial salts are included, i.e. salts with 1, 2 or 3, preferably 2, equivalents of base per mole of acid of the formula I or salts with 1, 2 or 3 equivalents, preferably 1 equivalent, of acid per mole of base of the formula I.

Pharmaceutically unsuitable salts can also be used for isolation or purification. Only the pharmaceutically acceptable, nontoxic salts are used therapeutically, and are therefore preferred.

The compounds of the formula I have valuable pharmacological properties. They have a high binding affinity toward excitatory amino acid receptors, such as toward AMPA receptors, NMDA (kainate) receptors and/or glycine binding sites of NMDA receptors. The affinity for the receptors mentioned is global or selective, depending on the structure. Selected compounds of the formula I in particular have a strong affinity for AMPA and/or NMDA (kainate) binding sites and a less strong affinity for glycine binding sites of the NMDA receptor.

The binding power of the compounds prepared according to the invention and their salts can be demonstrated radiographically in vitro on brain membranes of animals (mice, rats) by means of the displacement of [$^3$H]-AMPA, [$^3$H]-kainate, [$^3$H]-DCKA (5,7-dichlorokynurenic acid) or [$^3$H]-MDL 105,510, the concentration ($IC_{50}$) necessary for a 50% displacement being determined.

For the determination of the binding affinity for AMPA receptors, it is possible to use, for example, the radioreceptor assay experimental arrangement of Honore T., Lauridsen J. and Krogsgaard-Larsen according to J. Neurochem. 38, 173–178 (1981), in which compounds of the formula I show $IC_{50}$ values of approximately 0.05 to approximately 5 $\mu$M. The binding affinity for kainate receptors can be measured, for example, by means of the radioreceptor assay experimental arrangement of Simon J. R., Contrera J. F. and Kuhn M. J., J. Neurochem 26, 141–147 (1975), in which compounds of the formula I show $IC_{50}$ values of approximately 0.5 to approximately 5 $\mu$M.

The binding power of compounds of the formula I to glycine binding sites of the NMDA receptor can be determined, for example, in the radioreceptor assay experimental arrangement according to Baron M. B., Siegel B. W. et al., Eur. J. Pharmacol., Molec. Pharmacol. Section 206, pages 149–154 (1991) and Canton T., Doble A. et al., J. Pharm. Pharmacol. 44, pages 812–816 (1992) on rats' cortex and rat hippocampus membranes. The $IC_{50}$ value of compounds of the formula I in this experimental arrangement lies in the range from approximately 0.005 to approximately 5 $\mu$M.

On account of these properties, the compounds of the formula I have marked anticonvulsive properties, which are determined in vivo, for example on the mouse by means of their marked protective action toward convulsions induced by electroshock or metrazole, it being possible to use, for example, the established electroshock mouse model or the mouse model for metrazole-induced convulsions according to Schmutz et al., Naunyn-Schmiedeberg's Arch. Pharmacol. 342, 61–66 (1990).

The compounds of the formula I and their pharmaceutically acceptable salts are thus especially suitable for the prophylactic and therapeutic treatment of pathological conditions which respond to blockage of excitatory amino acid receptors, in particular blockage of one or more of the mentioned subtypes of excitatory amino acid receptors, for example of neurodegenerative disorders, such as of neurodegenerative disorders as a result of stroke, hypoglycemia, anoxia or cerebral palsy symptoms, of ischemic brain disorders, such as cerebral ischemia, cerebral ischemia in heart surgery or cardiac arrest, perinatal asphyxia, epileptic attacks, Huntington's chorea, Alzheimer's and Parkinson's disease, amyotropic lateral sclerosis, bone marrow and cerebral trauma and symptoms of poisoning by neurotoxins or addictive drug abuse, and of ischemic disorders of the eye, of vascular and muscle spasms, such as of migraine or of local or general spasticity, of convulsions, such as epilepsy, and of states of anxiety and pain, such as of trigeminal neuralgias.

The invention relates primarily to compounds of the formula I, in which $R_1$ is hydroxyl, lower alkyl, lower alkenyl, phenyl-lower alkyl, naphthyl-lower alkyl, phenyl or naphthyl, X is lower alkylene, lower alkylidene, oxo-lower alkylene, oxo-lower alkenylene, polyhalo-lower alkylidene, carboxy-lower alkylidene, hydroxy-lower alkylidene, lower alkoxy-lower alkylidene, lower alkylthio-lower alkylidene, 3- to 6-membered cycloalkylene, 3- to 6-membered cycloalkylidene, 3- to 6-membered benzocycloalkenylidene, 3- to 6-membered cycloalkyl-lower alkylene, 3- to 6-membered cycloalkyl-lower alkylidene, phenyl-lower alkylene, phenyl(oxo)-lower alkylene, phenyl-lower alkylidene, pyrrolyl-lower alkylidene, furyl-lower alkylidene, thienyl-lower alkylidene, pyridyl-lower alkylidene, phenylene or naphthylene, $R_2$ is hydrogen, lower alkyl, lower alkenyl, phenyl-lower alkyl or naphthyl-lower alkyl, where the ring system of the cycloalkylene, cycloalkylidene, unfused or benzofused cycloalkylene, cycloalkylidene or cycloalkenylidene, cycloalkyl-lower alkylidene, cycloalkyl-lower alkenylidene, phenyl-lower alkylene, phenyl(oxo)-lower alkylene, phenyl-lower alkylidene, furyl-lower alkylidene, thienyl-lower alkylidene, pyridyl-lower alkylidene, phenylene, naphthylene, phenyl-lower alkyl and naphthyl-lower alkyl radicals mentioned can be substituted by lower alkyl, lower alkoxy, phenoxy, hydroxyl, halogen, trifluoromethyl, di-lower alkylamino, lower alkanoylamino, nitro, carboxyl, lower alkoxycarbonyl, carbamoyl and/or cyano, alk is lower alkylidene and $R_3$, $R_4$ and $R_5$ independently of one another are hydrogen, lower alkyl, halogen, trifluoromethyl, cyano or nitro, and their salts.

The invention relates especially to compounds of the formula I, in which $R_1$ is hydroxyl, $C_1$–$C_4$alkyl, such as methyl or butyl, phenyl-$C_1$–$C_4$alkyl, such as benzyl, or phenyl, X is straight-chain or branched $C_1$–$C_4$alkylene, such as methylene or 1,2-ethylene, straight-chain or branched $C_1$–$C_4$alkylidene, such as 1,1-ethylene, 1,1- or 2,2-propylidene or 1,1-butylidene, oxo-$C_2$–$C_4$alkylene, such as, in particular, 1-oxoethylene or 1-oxopropylene, oxo-$C_3$–$C_4$alkenylene, such as 1-oxoprop-2-enylene or 1-oxobut-2-enylene, straight-chain or branched $C_1$–$C_4$alkylene, such as, in particular, methylene, polyhalo-$C_1$–$C_4$alkylidene, such as, in particular, 2,2,2-trifluoroethylidene, carboxy-$C_1$–$C_4$alkylidene, such as carboxymethylene, hydroxy-$C_2$–$C_4$alkylidene, such as 3-hydroxypropylidene or 4-hydroxybutylidene, 3- to 6-membered cycloalkylene, such as cyclopropylene or 1,2-cyclohexylene, 3- to 6-membered cycloalkylidene, such as cyclopropylidene or cyclohexylidene, 3- to 6-membered benzocycloalkenylidene, such as indan-2,2-ylidene, a phenyl(oxo)-$C_2$–$C_4$alkylene radical, such as a 1-oxo-2-phenylethylene radical, or phenyl-$C_1$–$C_4$alkylidene radical, such as a benzylidene radical, which is unsubstituted or substituted by $C_1$–$C_4$alkyl, such as methyl, $C_1$–$C_4$alkoxy, such as methoxy, phenoxy, hydroxyl, halogen of atomic number up to and including 35, such as fluorine, chlorine or bromine, trifluoromethyl, di-$C_1$–$C_4$alkylamino, such as dimethylamino, $C_1$–$C_7$alkanoylamino, such as acetylamino, nitro, carboxyl, $C_1$–$C_4$alkoxycarbonyl, such as methoxycarbonyl or ethoxycarbonyl, carbamoyl and/or cyano; pyrrolyl-$C_1$–$C_4$alkylidene, such as pyrrolylmethylene, furyl-$C_1$–$C_4$alkylidene, such as furylmethylene, thienyl-$C_1$–$C_4$alkylidene, such as thienylmethylene, or phenylene, $R_2$ is hydrogen, $C_1$–$C_4$alkyl, such as methyl, ethyl, propyl, isopropyl or butyl, phenyl-$C_1$–$C_4$alkyl, such as benzyl, which is unsubstituted or substituted by $C_1$–$C_4$alkyl, such as methyl, $C_1$–$C_4$alkoxy, such as methoxy, hydroxyl, halogen of atomic number up to and including 35, such as fluorine, chlorine or bromine, trifluoromethyl, nitro, carboxyl, $C_1$–$C_4$alkoxycarbonyl, such as methoxycarbonyl, carbamoyl and/or cyano, alk is $C_1$–$C_4$alkylidene, such as methylene or 1,1-ethylene, and $R_3$, $R_4$ and $R_5$ independently of one another are hydrogen, $C_1$–$C_4$alkyl, such as methyl or ethyl, halogen of atomic number up to and including 35, such as chlorine or bromine, trifluoromethyl, cyano or nitro, and their salts.

The invention relates in particular to compounds of the formula I, in which $R_1$ is hydroxyl, straight-chain or branched $C_1$–$C_4$alkylidene, such as methylene, ethylidene, ethylene, 1,1 - or 2,2-propylidene or 1,1-butylidene, straight-chain or branched $C_1$–$C_4$alkylene, such as ethylene, 1,2- or 1,3-propylene, 1,4- or 1,2-butylene, oxo-$C_2$–$C_4$alkylene, such as 1-oxoethylene or 1-oxopropylene, 3- to 6-membered cycloalkylene, such as cyclopropylene or 1,2-cyclohexylene, or 3- to 6-membered cycloalkylidene, such as cyclopropylidene or cyclohexylidene, $R_2$ is hydrogen or $C_1$–$C_4$alkyl, such as methyl, ethyl, propyl, isopropyl or butyl, alk is $C_1$–$C_4$alkylidene, such as methylene or 1,1-ethylene, and $R_3$, $R_4$ and $R_5$ independently of one another are hydrogen, $C_1$–$C_4$alkyl, such as methyl or ethyl, halogen of atomic number up to and including 35, such as chlorine or bromine, trifluoromethyl, cyano or nitro, and their salts.

The invention relates first and foremost to compounds of the formula I, in which $R_1$ is hydroxyl straight-chain or branched $C_1$–$C_4$alkylidene, such as methylene, ethylidene, ethylene, 1,1- or 2,2-propylidene or 1,1-butylidene, straight-chain or branched $C_1$–$C_4$alkylene, such as ethylene, 1,2- or 1,3-propylene, 1,4- or 1,2-butylene, 3- to 6-membered cycloalkylene, such as cyclopropylene or 1,2-cyclohexylene, or 3- to 6-membered cycloalkylidene, such as cyclopropylidene or cyclohexylidene, $R_2$ is hydrogen or $C_1$–$C_4$alkyl, such as methyl, ethyl, propyl, isopropyl or butyl, alk is $C_1$–$C_4$alkylidene, such as methylene, $R_4$ is hydrogen, $C_1$–$C_4$alkyl, such as methyl or ethyl, halogen of atomic number up to and including 35, such as chlorine or bromine, trifluoromethyl, cyano or nitro, and $R_3$ and $R_5$ are hydrogen, and their salts.

The invention relates namely to the compounds of the formula I mentioned in the examples and their salts, processes for their preparation, pharmaceutical preparations comprising them and their use as pharmaceutical active ingredients.

The process for the preparation of the compounds of the formula I comprises detaching, from a compound of the formula II

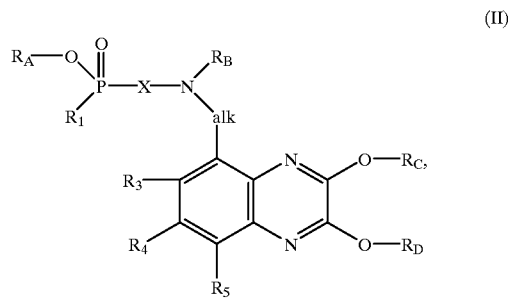

in which $R_A$ is hydrogen or a hydroxy protective group, $R_B$ is a group $R_2$ or an amino protective group and the radicals $R_C$ and $R_D$ are identical or different hydroxy protective groups and $R_1$, X, $R_2$, alk, $R_3$, $R_4$ and $R_5$ are as defined, the hydroxy protective groups $R_C$ and $R_D$ and a hydroxy protective group $R_A$ which may be present and an amino protective group $R_B$ which may be present and, if desired, in each case converting a compound obtained into another compound of the formula I, separating an isomer mixture obtainable according to the process into the components and separating off the preferred isomer in each case and/or converting a free compound obtainable according to the process into a salt or a salt obtainable according to the process into the corresponding free compound.

Suitable hydroxy protective groups RA are, for example, the hydroxy protective groups customary for the intermediate protection of phosphono groups, such as, in particular, lower alkyl, e.g. methyl, ethyl or isopropyl, furthermore substituted or unsubstituted phenyl-lower alkyl groups, such as benzyl groups, as well as tri-lower alkylsilyl, such as trimethylsilyl. Hydroxy protective groups $R_C$ and/or $R_D$ are, for example, the hydroxy protective groups customary for the intermediate protection of lactam groups, in particular ether-forming groups, such as lower alkyl, preferably methyl.

Suitable amino protective groups $R_3$ are, for example, the protective groups customary for the intermediate protection of amino groups, such as acyl groups derived from a hemiester of carbonic acid, such as lower alkoxycarbonyl or substituted or unsubstituted phenoxy- or phenyl-lower alkoxycarbonyl groups.

The detachment of the mentioned protective groups $R_C$, $R_D$ and, if desired, $R_A$ and/or $R_B$ is carried out in a customary manner, for example by acid treatment, such as treatment with hydrochloric acid, for example 1N to 4N hydrochloric acid, approximately 20% to approximately 40% hydrobromic acid in acetic acid, or treatment with a tri-lower alkyl halosilane, such as trimethylbromosilane, or a hexa-lower alkyldisilazane, such as hexamethyldisilazane, with subsequent addition of a lower alkanol, such as ethanol, which reacts with the silane component with release of hydrogen halide. Alternatively, the detachment of the protective group can also be carried out by treatment with a Lewis acid, such as a tri-lower alkylhalosilane, where, however, more drastic reaction conditions, such as temperatures in the range from approximately 50° C. to approximately 110° C., may be necessary.

Starting substances of the formula II are prepared, for example, by reducing, in an approriate compound of the formula III (III)

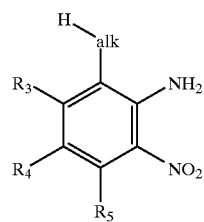

the nitro group to amino in a customary manner, for example by catalytic hydrogenation in the presence of palladium or Raney nickel, condensing the resulting phenylene-1,2-diamine under acidic conditions, for example in the presence of hydrochloric acid, with oxalic acid to give the corresponding quinoxalinedione of the formula IV (IV)

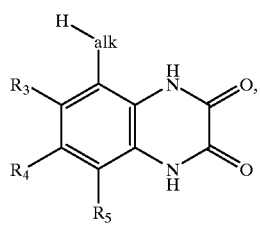

converting this by reaction with a halogenating agent introducing a halogen Hal, for example phosphorus oxychloride, into the corresponding 2,3-dihaloquinoxaline of the formula V (V)

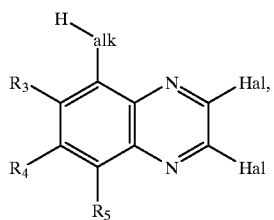

replacing the groups Hal in this in a customary manner, for example by reaction with an alkali metal lower alkanolate, such as sodium methanolate, by protected hydroxyl —$OR_C$ or —$OR_D$, such as lower alkoxy, in particular methoxy, halogenating the resulting compound of the formula VI (VI)

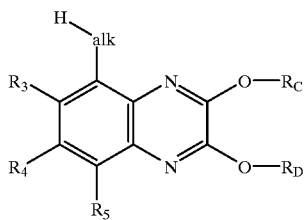

with a halogenating agent introducing a halogen Hal, such as N-bromosuccinimide, in the presence of azoisobutyronitrile or dibenzoyl peroxide, in the side chain to give the corresponding compound of the formula VII (VII)

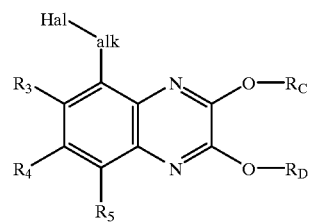

and converting this by reaction with an azide, such as sodium azide, and subsequent reduction, for example treatment with triphenylphosphine and water, into the corresponding amino compound of the formula VIII (VIII)

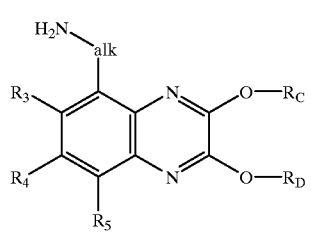

and condensing this either with a carbonyl compound of the formula H-X=O (IX) and then in the presence of a base, such as tri-lower alkylamine, with a tri-lower alkylsilyl ether, such as the trimethylsilyl ether, of a compound of the formula X (X)

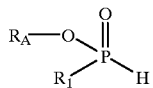

or in the presence of sodium cyanoborohydride directly with a compound of the formula XI (XI)

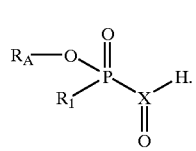

This process variant is particularly suitable for the preparation of compounds of the formula I in which X is a divalent aliphatic, cycloaliphatic-aliphatic, araliphatic, or heteroaryl-aliphatic radical.

In an advantageous modification of this process variant for the preparation of compounds of the formula I in which X is lower alkylidene, in particular methylene, the amine of the formula X is converted with formaldehyde or a formaldehyde-donating agent into the corresponding triazinan of the formula XII

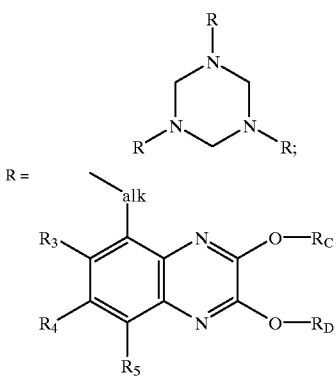

and reacting this, for example in the presence of a base, such as a tri-lower alkylamine, with a tri-lower alkylsilyl ether, such as the trimethylsilyl ether, of the compounds of the formula X.

For the preparation of compounds of the formula II in which X bears an oxo group in the α-position to the amino group, the amine compound VIII is advantageously reacted in the presence of a dehydrating agent, such as of a carbodiimide, e.g. of N-(dimethylaminopropyl)-N'-ethylcarbodiimide hydrochloride, with an appropriate carboxylic acid compound of the formula XIII

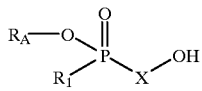

or, in the presence of a basic condensing agent, with a reactive derivative thereof, such as an acid halide or reactive ester.

For the preparation of compounds of the formula II in which X is a divalent cycloaliphatic or aromatic radical, halogen compounds of the formula VII are advantageously used as starting materials and these are condensed in a customary manner with an appropriate amine component of the formula XIV

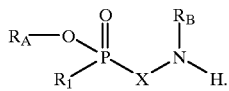

Compounds obtainable according to the process can be converted into other compounds of the formula I in a customary manner.

Thus aliphatic or araliphatic radicals, such as lower alkyl, lower alkenyl or lower alkanoyl radicals, can be introduced in a customary manner into compounds of the formula I in which $R_2$ is hydrogen, for example by reaction with a lower alkylating agent, such as a lower alkyl halide or a reactive lower alkanoic acid derivative, such as a lower alkanoyl chloride, if necessary in the presence of a customary basic condensing agent.

Furthermore, compounds of the formula I comprising esterified or amidated carboxyl groups can be hydrolyzed to the corresponding carboxylic acids in a customary manner, or compounds of the formula I comprising free carboxyl can be esterified or amidated in the customary manner.

Furthermore, cyano can be converted into carbamoyl in a customary manner in compounds of the formula I obtained.

Salts obtained can be converted into the free compounds in a manner known per se, e.g. by treating with a base, such as an alkali metal hydroxide, a metal carbonate or hydrogencarbonate, or another salt-forming base mentioned at the outset, or with an acid, such as a mineral acid, e.g. with hydrogen chloride, or another salt-forming acid mentioned at the outset.

Salts obtained can be converted into other salts in a manner known per se, acid addition salts, for example, by treating with a suitable metal salt, such as a sodium, barium or silver salt, of another acid in a suitable solvent in which an inorganic salt formed is insoluble and thus is eliminated from the reaction equilibrium, and base salts by setting free the free acid and fresh salification.

The compounds of the formula I, including their salts, can also be obtained in the form of hydrates or include the solvent used for crystallization.

As a result of the close relationship between the novel compounds in free form and in the form of their salts, above and below the free compounds and their salts are analogously and expediently to be understood as meaning, if desired, also the corresponding salts or free compounds.

On account of the physicochemical differences in the constituents, diastereomer mixtures and racemate mixtures obtained can be separated into the pure diastereomers or racemates in a known manner, for example by chromatography and/or fractional crystallization.

Racemates obtained can furthermore be resolved into the optical antipodes, for example by recrystallization from an optically active solvent, with the aid of microorganisms or by reaction of the resulting diastereomer mixture or racemate with an optically active auxiliary compound, e.g. according to the acidic, basic or functionally modifiable groups contained in compounds of the formula I with an optically active acid, base or an optically active alcohol, to give mixtures of diastereomeric salts or functional derivatives, such as esters, and separation thereof into the diastereomers, from which the desired enantiomer in each case can be released in the manner customary in each case. Bases, acids or alcohols suitable for this, are, for example, optically active alkaloid bases, such as strychnine, cinchonine or brucine, or D- or L-(1-phenyl)ethylamine, 3-pipecoline, ephedrine, amphetamine and similar synthetically accessible bases, optically active carboxylic or sulfonic acids, such as quinic acid or D- or L-tartaric acid, D- or L-di-o-toluyltartaric acid, D- or L-malic acid, D- or L-mandelic acid, or D- or L-camphorsulfonic acid, or optically active alcohols, such as borneol or D- or L-(1-phenyl) ethanol.

The invention also relates to those embodiments of the process according to which a compound obtainable as an intermediate in any stage of the process is used as a starting compound and the missing steps are carried out or a starting substance is used in the form of a salt or, in particular, formed under the reaction conditions.

The novel starting substances, which were developed especially for the preparation of the compounds according to the invention, in particular the selection of starting substances leading to compounds of the formula I marked as preferred at the outset, the processes for their preparation and their use as intermediates likewise form a subject of the invention.

The pharmaceutical preparations according to the invention, which contain the compound according to the invention or pharmaceutically acceptable salts thereof, are those for enteral, such as oral, furthermore rectal, and parenteral administration to (a) warm-blooded animal(s) the pharmacological active ingredient being contained on its own or together with a pharmaceutically acceptable carrier. The daily dose of the active ingredient depends on the age and the condition of the individual and on the manner of administration.

The novel pharmaceutical preparations contain, for example, from approximately 10% to approximately 80%, preferably from approximately 20% to approximately 60%, of the active ingredient. Pharmaceutical preparations according to the invention for enteral or parenteral administration are, for example, those in unit dose forms, such as sugar coated tablets, tablets, capsules or suppositories, and furthermore ampoules. These are prepared in a manner known per se, e.g. by means of conventional mixing, granulating, sugar-coating, dissolving or lyophilizing processes. Thus, pharmaceutical preparations for oral use can be obtained by combining the active ingredient with solid carriers, if desired granulating a resulting mixture, and processing the mixture or granules, if desired or necessary, to give tablets or sugar-coated cores after addition of suitable adjuncts.

Suitable carriers are, in particular, fillers, such as sugars, e.g. lactose, sucrose, mannitol or sorbitol, cellulose preparations and/or calcium phosphates, e.g. tricalcium phosphate or calcium hydrogenphosphate, furthermore binders, such as starch pastes, using, for example, corn, wheat, rice or potato starch, gelatin, tragacanth, methylcellulose and/or polyvinylpyrrolidone, if desired, disintegrants, such as the abovementioned starches, furthermore carboxymethylstarch, crosslinked polyvinylpyrrolidone, agar, alginic acid or a salt thereof, such as sodium alginate, adjuncts are primarily flow, flow-regulating and lubricating agents, e.g. silicic acid, talc, stearic acid or salts thereof, such as magnesium or calcium stearates, and/or polyethylene glycol. Sugar-coated cores are provided with suitable coatings, which may be enteric, using, inter alia, concentrated sugar solutions which may contain gum arabic, talc, polyvinylpyrrolidone, polyethylene glycol and/or titanium dioxide, lacquer solutions in suitable organic solvents or solvent mixtures or, for the preparation of enteric coatings, solutions of suitable cellulose preparations, such as acetylcellulose phthalate or hydroxypropylmethylcellulose phthalate. Colorants or pigments, e.g. for the identification or for the marking of various active ingredient doses, can be admixed to the tablets or sugar-coated tablet coatings.

Further orally administrable pharmaceutical preparations are hard capsules made of gelatin, and soft, closed capsules made of gelatin and a plasticizer, such as glycerol or sorbitol. The hard capsules can contain the active ingredient in the form of granules, e.g. as a mixture with fillers, such as lactose, binders, such as starches, and/or lubricants, such as talc or magnesium stearate, and, if desired, stabilizers. In soft capsules, the active ingredient is preferably dissolved or suspended in suitable liquids, such as fatty oils, liquid paraffin or liquid polyethylene glycols, it also being possible to add stabilizers.

Suitable rectally administrable pharmaceutical preparations are, for example, suppositories which consist of a combination of the active ingredient with a suppository base. Suitable suppository bases are, for example, natural or synthetic triglycerides, paraffin hydrocarbons, polyethylene glycols or higher alkanols. Furthermore, it is also possible to use gelatin rectal capsules which contain a combination of the active ingredient with a base material. Possible base materials are, for example, liquid triglycerides, polyethylene glycols or paraffin hydrocarbons.

For parenteral administration, aqueous solutions of an active ingredient in water-soluble form are primarily suitable, e.g. of a water-soluble salt, furthermore suspensions of the active ingredients, such as appropriate oily injection vehicles, such suitable lipophilic solvents or vehicles, such as fatty oils, e.g. sesame oil, or synthetic fatty acid esters, e.g. ethyl oleate or triglycerides, being used or aqueous injection suspensions which contain viscosity-increasing substances, e.g. sodium carboxymethylcellulose, sorbitol and/or dextran, and, if desired, also stabilizers.

The dose of the active ingredient depends on the warm-blooded species, the age and the condition of the individual and the manner of administration. In the normal case, an approximate daily dose of about 10 mg to about 500 mg is to be estimated in the case of oral administration for a patient weighing about 75 kg.

The following examples serve to illustrate the invention; temperatures are indicated in degrees Celsius, pressures in mbar.

EXAMPLE 1

N-Acetyl-N-(7-bromo-2,3-dioxo-1,2,3,4-tetrahydroquinoxalin-5-ylmethyl) aminomethylphosphonic acid 400 mg (0.87 mmol) of dimethyl N-acetyl-N-(7-bromo-2,3-dimethoxyquinoxalin-5-ylmethyl)-α-aminomethylphosphonate are dissolved in 5 ml of absolute dichloromethane under a nitrogen atmosphere and treated with 0.66 ml (5 mmol) of trimethylsilyl bromide at room temperature. After stirring at room temperature for 16 hours, 5 ml of ethanol are added and the mixture is stirred at room temperature for a further 6 hours. It is then concentrated to dryness. The residue is taken up in ethyl acetate, treated with hexane to slight turbidity and allowed to stand overnight in a refrigerator. The precipitate is filtered off, dried in a high vacuum and, for further purification, dissolved in 10 ml of water and dilute sodium hydroxide solution at pH 10. The solution is adjusted to pH 1 with 2N hydrochloric acid and allowed to stand overnight in a refrigerator, whereupon a colorless precipitate is formed which, filtered off and dried, affords 134 mg (0.33 mmol) of the title compound; m.p.>280°.

The starting material can be prepared, for example, in the following manner:

a) 5-Bromo-2,3-diaminotoluene

A solution of 15 g (64.9 mmol) of 4-bromo-2-methyl-6-nitroaniline in 300 ml of ethanol is hydrogenated at about 27° for 4 hours in the presence of 1.5 g of Raney nickel. The reaction mixture is then filtered and evaporated. The title compound is obtained as a brown oil.

$^1$H-NMR (250 MHz, CDCl$_3$); δ=6.76, 6.73 (2d, 2H), 3.22 (s, 2NH$_2$), 2.14 (s,Me).

b) 7-Bromo-5-methyl-1,2,3,4-tetrahydroquinoxalin-2,3-dione 13.05 g (64.9 mmol) of 5-bromo-2,3-diaminotoluene and 6.42 g (1.1 eq.) of oxalic acid are stirred under reflux for 16 hours in 2N hydrochloric acid. The mixture is cooled, and the solid is filtered off and washed with water. The title compound is obtained as a brown solid.

$^1$H-NMR (250 MHz, DMSO); δ==11.98, 11.32 (2s, 2NH), 7.13 (s, 2H), 2.33 (s, Me).

c) 7-Bromo-2,3-dichloro-5-methylquinoxaline 17 g (66.6 mmol) of 7-bromo-5-methyl-1,2,3,4-tetrahydroquinoxalin-2,3-dione are stirred under reflux for 5 hours and at 20° for 40 hours in 80 ml of phosphorus oxychloride. The mixture is evaporated and dried under a high vacuum. The residue is cautiously treated with a saturated potassium carbonate solution, and the solid is filtered off and washed with water. The title compound is obtained as a brown solid.

$^1$H-NMR (250 MHz, DMSO); δ=8.16, 7.99 (2d, 2H), 2.63 (s, Me).

d) 7-Bromo-5-methyl-2,3-dimethoxyguinoxaline 2.97 g (129.5 mmol) of sodium are dissolved in 100 ml of methanol. This solution is added to 18.9 g (64.7 mmol) of 7-bromo-5-methyl-2,3-dichloroquinoxaline in 60 ml of methanol and heated to reflux for 20 hours. The mixture is cooled and treated with 15 ml of water. The solid is filtered off and washed with methanol and water. The title compound is obtained as a beige solid.

$^1$H-NMR (250 MHz, DMSO); δ=7.73, 7.58 (2d, 2H), 4.05, 4.03 (2s, 2Me), 2.58 (s, Me).

e) 7-Bromo-5-bromomethyl-2,3-dimethoxyguinoxaline 15 g (53 mmol) of 7-bromo-5-methyl-2,3-dimethoxyquinoxaline, 9.9 g (1.05 eq.) of N-bromosuccinimide and 0.87 g (0.1 eq.) of azoisobutyronitrile are dissolved in 100 ml of carbon tetrachloride and stirred under reflux for 24 hours. The solid is filtered off and the filtrate is diluted with dichloromethane. It is washed once each with water and brine. The organic phase is dried over magnesium sulfate and evaporated. The residue is recrystallized using ethyl acetate and hexane. The title compound is obtained as slightly orange crystals.

$^1$H-NMR (250 MHz, CDCl$_3$); δ=7.90, 7.68 (2d, 2H), 4.95 (s, 2H), 4.20, 4.13 (2s, 2Me).

f) 5-Azidomethyl-7-bromo-2,3-dimethoxyquinoxaline 743 mg (2 eq.) of sodium azide are added at 20° to 2.07 g (5.72 mmol) of 7-bromo-5-bromomethyl-2,3-dimethoxyquinoxaline in 25 ml of dimethylformamide. After 3 hours, the mixture is poured into water, extracted with diethyl ether, and the extract is washed with water and brine and dried using magnesium sulfate. The solvent is evaporated.

$^1$H-NMR (250 MHz, CDCl$_3$); δ=7.92, 7.58 (2d, 2H), 4.80 (s, 2H), 4.18, 4.13 (2s, 2Me).

g) 5-Aminomethyl-7-bromo-2,3-dimethoxyguinoxaline 4.47 g (13.8 mmol) of 5-azidomethyl-7-bromo-2,3-dimethoxyquinoxaline are dissolved in 35 ml of tetrahydrofuran and 3.98 g (1.1 eq.) of triphenylphosphine are added. The mixture is stirred at 20° for 4 hours. 746 mg of water are added and the mixture is stirred for a further 3 hours. The solid is filtered off and the filtrate is extracted with ethyl acetate and sodium carbonate solution. The organic phases are combined, washed with brine, dried over magnesium sulfate and evaporated. The residue is chromatographed on silica gel using ethyl acetate/petroleum ether 1:1.

1H-NMR (250 MHz, CDCl$_3$); δ=7.85, 7.53 (2d, 2H), 4.22 (s, 2H), 4.12 (s, 2Me).

h) 1,3,5-Tri-N-(7-bromo-2,3-dimethoxyquinoxalin-5-ylmethyl)-[1,3,5]-triazinan 2.98 g (10 mmol) of (7-bromo-2,3-dimethoxyquinoxalin-5-ylmethyl)amine are dissolved in 40 ml of ethanol by warming. After cooling to room temperature, 1 ml of formalin solution (37% in water) is added dropwise to the slightly yellow solution. After addition is complete, the product is deposited in the form of a colorless precipitate. After stirring for 3 hours, the precipitate is filtered off. After drying in a high vacuum, the title compound is obtained as a colorless amorphous crystalline mass.

$^1$H-NMR (300 MHz, CDCl$_3$); δ=7.83 (d, 2.3 Hz, 3H), 7.72 (d, 2.3 Hz, 3H), 4.24 (s, 6H), 4.13 (s, 9H), 4.04 (s, 9H), 3.69 (br. s, 6H). MS(FAB): 930, 932 i) Dimethyl N-(7-bromo-2,3-dimethoxyquinoxalin-5-ylmethyl)aminomethylphosphonate 975 ml (10.64 mmol) of dimethyl phosphite, 1.27 ml (9.19 mmol) of triethylamine and 1.47 ml (11.6 mmol) of trimethylsilyl chloride are stirred in 200 ml of chloroform under a nitrogen atmosphere for 90 minutes. In the course of one hour, the solution is added dropwise at 0° to 3.0 g (3.22 mmol) of 1,3,5-tri-N-(7-bromo-2,3-dimethoxyquinoxalin-5-ylmethyl)-[1,3,5]-triazinan dissolved in 200 ml of chloroform. After stirring at room temperature for 16 h, the suspension is poured onto ice-cold hydrochloric acid (0.1N in water) and treated with 3 parts of ether. The organic phase is exhaustively extracted by shaking with 0.1N aqueous hydrochloric acid. The combined aqueous phases are adjusted to pH 12–13 with potassium carbonate solution and extracted 6 times with dichloromethane. After drying over sodium sulfate and concentrating the organic phase, 3.65 g of slightly yellow-colored crystals of the title compound are obtained.

$^1$H-NMR (300 MHz, CDCl$_3$); δ=7.88 (d, 2.3 Hz, $^1$H), 7.54 (d, 2.3 Hz, $^1$H), 4.25 (s, 2H), 4.15 (s, 3H), 4.14 (s, 3H), 3.78 (d, 10 Hz, 6H), 2.95 (d, 13.1 Hz, 2H), MS(ES$^+$) 422, 420 (MH$^+$)

j) Dimethyl N-acetyl-N-(7-bromo-2,3-dimethoxyquinoxalin-5-ylmethyl)aminomethylphosphonate The solution of 420 mg (1 mmol) of dimethyl N-(7-bromo-2,3-dimethoxyquinoxalin-5-ylmethyl)-α-aminophosphonate in 15 ml of tetrahydrofuran cooled to 0° is successively treated with 0.18 ml (1.3 mmol) of triethylamine and 0.13 ml (1.1 mmol) of acetyl chloride. The colorless suspension is stirred for 16 h at firstly 0° and then at room temperature and finally concentrated. The residue is taken up in dichloromethane and washed with 0.1N hydrochloric acid. The organic phase is dried over sodium sulfate, concentrated and purified on a silica gel column using ethyl acetate as eluent. After concentrating and drying, 400 mg (0.87 mmol) of the title compound are isolated as a colorless oil.

$^1$H-NMR (300 MHz, CDCl$_3$); δ=7.91 (d, 2.2 Hz, 0.7H), 7.89 (d, 2.3 Hz, 0.3H), 7.59 (d, 2.3 Hz, 0.3H), 7.32 (d, 2.2 Hz, 0.7H), 5.22 (s, 0.6H), 5.20 (s, 1.4H), 4.16 (s, 0.9H), 4.14 (s, 4.2H), 4.13 (s, 0.9H), 3.92 (d, 11.2 Hz, 1.4H), 3.82 (d, 10.8 Hz, 1.8H), 3.79 (d, 10.9 Hz, 4.2H), 3.78 (d, 14.2 Hz, 0.6H), 2.27 (s, 0.6H), 2.20 (s, 1.4H), MS(ES$^+$) 464, 462 (MH$^+$)

EXAMPLE 2

N-Acetyl-N-(7-chloro-2,3-dioxo-1,2,3,4-tetrahydroquinoxalin-5-ylmethyl) aminomethylphosphonic acid The title compound can be prepared in a manner analogous to that described under Example 1. The intermediate 5-bromomethyl-7-chloro-2,3-dimethoxyquinoxaline to be employed in stage 1f) can be prepared, for example, in the following manner:

a) 7-Chloro-5-methyl-1,4-dihydroquinoxalin-2,3-dione 123 g (0.79 mol) of 2,3-diamino-5-chlorotoluene and 106.2 g (1.18 mol) of oxalic acid are heated at reflux for 5 hours in 800 ml of 4N hydrochloric acid. The reaction mixture is allowed to cool, and is diluted with water, filtered off on a suction filter and washed with water. The product is then stirred in hot ethanol, filtered off on a suction filter and the suction filter material is dried in vacuo at 60°. The title compound is obtained as slightly grayish crystals of m.p.>250°.

b) 2,3,7-Trichloro-5-methylquinoxaline 155 g (0.74 mol) of 7-chloro-5-methyl-1,4-dihydroquinoxaline-2,3-dione and 321.8 g (1.55 mol) of phosphorus pentachloride are stirred at reflux for 36 hours in 950 ml of phosphorus oxychloride. The phosphorus oxychloride is distilled off and the residue is poured onto 3 l of ice-water. The resulting suspension is stirred, filtered off on a suction filter and washed with water. After drying the suction filter material in vacuo at 60°, the title compound is obtained as brownish crystals, which are used without further purification.

c) 7-Chloro-2,3-dimethoxy-5-methylquinoxaline 30 g (0.121 mol) of 2,3,7-trichloro-5-methylquinoxaline are introduced into 330 ml of methanol under argon at room temperature. 67.9 ml (0.364 mmol) of an about 5.4 molar solution of sodium methoxide in methanol is added dropwise to this and the mixture is stirred at reflux for 4.5 hours. After cooling to 0° C., the suspension is filtered off on a suction filter, and the filter residue is washed with methanol and dried in vacuo at 60° C. The title compound is obtained as brownish crystals of m.p. 94–96° C.

d) 5-Bromomethyl-7-chloro-2,3-dimethoxyguinoxaline 10.0 g (41.9 mmol) of 7-chloro-2,3-dimethoxy-5-methylquinoxaline are introduced into 160 ml of chlorobenzene under argon at room temperature. 8.6 g (48.2 mmol) of N-bromosuccinimide and 0.69 g (4.2 mmol) of azoisobutyronitrile are added and the mixture is stirred at 80° C. for 18 hours. After cooling the reaction mixture to room temperature, the chlorobenzene is distilled off, the residue is treated with diethyl ether and the resulting suspension is filtered off on a suction filter. The filtrate is concentrated, the residue is crystallized from n-hexane and the title compound is obtained as colorless crystals of m.p. 114–116°.

EXAMPLE 3

N-Acetyl-N-(7-fluoro-2,3-dioxo-1,2,3,4-tetrahydroquinoxalin-5-ylmethyl) aminomethylphosphonic acid The title compound can be prepared in a manner analogous to that described under Example 1. The intermediate 5-aminomethyl-7-fluoro-2,3-dimethoxyquinoxaline to be employed in stage g) can be prepared, for example, in the following manner:

a) 2,3-Diamino-5-fluorotoluene 25 g (0.147 mol) of 4-fluoro-2-methyl-6-nitroaniline in 250 ml of tetrahydrofuran are hydrogenated at about 34° C. for 2 hours in the presence of 8 g of Raney nickel. The reaction mixture is then filtered off and concentrated. The title compound is obtained as a brown oil.

$^1$H-NMR (200 MHz, CDCl$_3$); δ=6.32–6.38 (2H), 3.25 (s, 2NH$_2$), 2.1 (s, Me).

b) 7-Fluoro-5-methyl-1,2,3,4-tetrahydroquinoxaline-2,3-dione 20 g (0.118 mol) of 2,3-diamino-5-fluorotoluene and 15.8 g (0.176 mol) of oxalic acid are stirred at reflux for 16 hours in 4N hydrochloric acid. The reaction mixture is cooled, diluted with water, filtered off on a suction filter and washed with water. The title compound is obtained as beige crystals of m.p.>300° C.

c) 2,3-Dichloro-7-fluoro-5-methylquinoxaline 25 g (0.129 mol) of 7-fluoro-5-methyl-1,2,3,4-tetrahydroquinoxaline-2,3-dione are introduced into 170 mol of phosphorus oxychloride. 56.3 g (0.27 mol) of phosphorus pentachloride are added to this and the mixture is stirred under reflux for 16 hours. Excess phosphorus oxychloride is removed from the reaction mixture by distillation. The dark-brown residue is cooled and poured onto 1000 ml of ice-water. The suspension is filtered off on a suction filter, washed with plenty of water and the suction filter material is dried in vacuo at 60° C. The title compound is obtained as brown crystals of m.p. 116–120° C.

d) 7-Fluoro-5-methyl-2,3-dimethoxyquinoxaline 14 g (60.6 mmol) of 2,3-dichloro-7-fluoro-5-methylquinoxaline are introduced into 165 ml of methanol. An about 5.4M solution of sodium methanolate in methanol is added dropwise. The mixture is heated to reflux and stirred for 18 hours. The reaction mixture is cooled to 0° C., the suspension is filtered off on a suction filter and washed with cold methanol, and the filter material is dried in vacuo at 60° C. The crude product is recrystallized from hexane. The title compound is obtained as white crystals of m.p. 107–109° C.

e) 5-Bromomethyl-2,3-dimethoxy-7-fluoroquinoxaline 8.4 g (37.8 mmol) of 2,3-dimethoxy-7-fluoro-5-methylquinoxaline, 7.4 g (41.6 mmol) of N-bromosuccinimide and 0.63 g (0.38 mmol) of azoisobutyronitrile are introduced into 140 ml of carbon tetrachloride and stirred at reflux for 6 hours. The reaction mixture is cooled and concentrated, and the residue is taken up in diethyl ether. The suspension is filtered off and the mother liquor is concentrated again. The remaining crude product is recrystallized from hexane. The title compound is obtained as white crystals of m.p. 122–125° C.

f) 5-Azidomethyl-2,3-dimethoxy-7-fluoroquinoxaline 1.73 g (26.6 mmol) of sodium azide are added at room temperature to 4.0 g (13.3 mmol) of 5-bromomethyl-2,3-dimethoxy-7-fluoroquinoxaline in 50 ml of dimethylformamide and stirred for 5 h. The reaction mixture is poured onto water, extracted with diethyl ether and washed with water and brine. The organic phase is dried using Na$_2$SO$_4$, filtered off on a suction filter and concentrated. The title compound is obtained as white crystals of m.p. 75–78° C.

g) 5-Aminomethyl-2,3-dimethoxy-7-fluoroquinoxaline 3.5 g (13.3 mmol) of 5-azidomethyl-2,3-dimethoxy-7-fluoroquinoxaline in 35 ml of tetrahydrofuran are hydrogenated at room temperature for about 19 hours in the presence of 1.75 g of Raney nickel. The reaction mixture is filtered off and concentrated. The title compound is obtained as yellowish crystals.

$^1$H-NMR (300 MHz, DMSO); δ=7.3–7.5 (2H), 4.15 (s, 2H), 4.02 (s, 6H).

EXAMPLE 4

N-(2,3-Dioxo-7-nitro-1,2,3,4-tetrahydroquinoxalin-5-ylmethyl)-α-(ethylamino)ethylphosphonic acid hydrobromide 160 mg (0.37 mmol) of dimethyl N-(7-nitro-2,3-dimethoxyquinoxalin-5-ylmethyl)-α-(ethylamino) ethylphosphonate are dissolved in 8 ml of dichloromethane and stirred at room temperature for one hour with 0.19 ml (4 eq.) of triethylbromosilane. The solvent and excess reagent are evaporated and the residue is briefly dried in a high vacuum, dissolved in 5 ml of an about 33% hydrogen bromide solution in acetic acid, and stirred at room temperature for 18 hours. The reaction mixture is diluted with diethyl ether, and the solid is filtered off, washed with diethyl ether and dried. The title compound is obtained as a beige solid; m.p.=191° (dec.).

The starting material can be prepared, for example, in the following manner:

a1) 5-Bromomethyl-2,3-dimethoxyquinoxaline

The title compound can be prepared from 5-methyl-2,3-dioxo-1,2,3,4-tetrahydroquinoxaline in a manner analogous to that described under Example 1c, 1d, 1e.

b1) 5-Bromomethyl-7-nitro-2,3-dimethoxyquinoxaline 25 ml of sulfuric acid are cooled to 0° C. and 9.5 g (33.55 mmol) of 5-bromomethyl-2,3-dimethoxyquinoxaline are then added. After a further 10 minutes, 3.39 ml (1 eq.) of isopropyl nitrate are added and the mixture is stirred at 0° C. for 1 hour. The mixture is poured onto ice, and the solid is filtered off and washed with water. The title compound is obtained as a beige solid.

$^1$H-NMR (250 MHz, d$_6$-DMSO);δ=8.62, 8.40 (2d, 2H), 5.02 (s, 2H), 4.27, 4.19 (2s, 2Me).

c1) 5-[Di-( tert-butoxycarbonyl)amino]methyl-7-nitro-2,3-dimethoxyguinoxaline 10 g (30.5 mmol) of 5-bromomethyl-7-nitro-2,3-dimethoxyquinoxaline are dissolved in 50 ml of dimethylformamide. 7.3 g (1.1 eq.) of di-tert-butyl iminodicarboxylate and 14.9 g (1.5 eq.) of cesium carbonate are added and the reaction mixture is heated at 50° for 10 hours, then cooled to room temperature and extracted with water and ethyl acetate. The combined organic phases are dried over magnesium sulfate and concentrated. After column chromatography using hexane/ethyl acetate (9:1), the title compound is obtained as a yellow oil.

$^1$H-NMR (CDCl$_3$, 250 MHz); δ=8.55, 8.08 (2d, 2H); 5.34 (s, 2H), 5.34 (s, 2H), 4.18, 4.16 (2s, 2Me); 1.47 (s, 2 t-Bu).

d1) 5-Aminomethyl-7-nitro-2,3-dimethoxyquinoxaline 13.8 9 (29.7 mmol) of 5-[di-(tert-butoxycarbonyl)amino] methyl-7-nitro-2,3-dimethoxyquinoxaline are stirred at room temperature for 8 hours in 60 ml of trifluoroacetic acid. The reaction mixture is concentrated under reduced pressure and the red oil is well stirred at 0° for one hour with 1N potassium carbonate. The yellow crystals are filtered off, washed with 100 ml of water and 100 ml of a 1:1 mixture of ethyl acetate and hexane, and dried.

$^1$H-NMR (CDCl$_3$, 250 MHz); δ=8.57, 8.29 (2d, 2H); 4.33 (s, 2H); 4.20, 4.18 (2d, 2Me).

e1) Dimethyl N-(7-Nitro-2,3-dimethoxyquinoxalin-5-ylmethyl)-α-aminoethylphosphonate 500 mg (1.9 mmol) of 5-aminomethyl-7-nitro-2,3-dimethoxyquinoxaline, 834 mg (3.7 eq.) of magnesium sulfate, 335 mg (1.3 eq.) of potassium carbonate and 0.214 ml (2 eq.) of acetaldehyde are stirred at room temperature for 7 hours in 15 ml of dichloromethane. The reaction mixture is filtered off and the filtrate is evaporated. A solution of 0.32 ml (1.2 eq.) of triethylamine, 0.182 ml of dimethyl phosphite and 0.36 ml (1.5 eq.) of trimethylchlorosilane in 10 ml of dichloromethane is stirred at 0° for one hour, and the residue is added to 10 ml of dichloromethane and stirred for 14 hours. Water is added to the reaction mixture and the organic phase is separated off. The aqueous phase is extracted twice with dichloromethane and the combined organic phases are dried over magnesium sulfate. The title compound is obtained as a yellow resin after evaporation of the solvent.

$^1$H-NMR (CDCl$_3$, 250 MHz); δ=8.58, 8.34 (2d, 2H); 4.42, 4.34 (2d, 2H); 4.22, 4.19 (2d, 2Me); 3.82, 3.80 (2d, 2Me); 3.04 (m, $^1$H); 1.38 (dd, Me).

Dimethyl N-(7-Nitro-2,3-dimethoxyquinoxalin-5-ylmethyl)-α-aminoethylphosphonate can alternatively be prepared in the following manner:

a2) 2,3-Dimethoxyquinoxaline-5-carbaldehyde 17 ml (188 mmol) of 2-nitropropane are added to a solution of 3.7 g (163 mmol) of sodium in 700 ml of methanol. After stirring for 5 minutes, 35.5 g (125.4 mmol) of solid 5-bromomethyl-2,3-dimethoxyquinoxaline are added. The mixture is heated to reflux for 1 hour, a homogeneous solution resulting. After cooling, the solution is concentrated under reduced pressure. The residue is taken up in ethyl acetate and 1N hydrochloric acid, the phases are separated and the organic phase is washed with water and brine, dried over sodium sulfate and concentrated. The title compound is isolated in the form of white crystals by crystallization from ethyl acetate. M.p. 137–140°; TLC (ethyl acetate/hexane 1:3): R$_f$=0.45.

b2) 2,3-Dimethoxy-7-nitroquinoxaline-5-carbaldehyde 44 ml of 100% nitric acid, 44 ml of 97% sulfuric acid and 44 ml of trifluoroacetic anhydride are added successively to a solution of 22 g (100.8 mmol) of 5-bromomethyl-2,3-dimethoxyquinoxaline in 88 ml of trifluoroacetic acid cooled to 0°. The mixture is kept at 0° for 2 hours and then cautiously poured onto a mixture of 4N sodium hydroxide solution and ice. The temperature should not rise above 20°. The mixture is extracted with ethyl acetate, and the organic phase is washed with an aqueous 1N sodium hydroxide solution, water and brine and dried over sodium sulfate. Crystallization of the crude product affords 18.8 g of the title compound as slightly yellow crystals. M.p.=147–149°; TLC (SiO$_2$, EtOAc/hexane 1:3): R$_f$=0.25.

c2) Dimethyl N-(7-nitro-2,3-dimethoxyquinoxalin-5-ylmethyl)-α-aminoethylphosphonate 150 mg (0.569 mmol) of 2,3-dimethoxy-7-nitroquinoxaline-5-carbaldehyde, 90 mg (1.04 eq.) of dimethyl α-aminoethylphosphonate and 500 mg (7.3 eq.) of magnesium sulfate are dissolved in 5 ml of DMSO and stirred at room temperature for 24 hours. The reaction mixture is filtered off, the filtrate is evaporated and the residue is dissolved in 5 ml of methanol. 0.027 ml (1 eq.) of acetic acid, 78 mg (2 eq.) of sodium acetate and 36 mg (1.2 eq.) of sodium cyanoborohydride are added and the mixture is stirred at room temperature for 48 hours. The reaction mixture is treated with 1N hydrochloric acid, stirred for 30 minutes and then washed with diethyl ether. The aqueous phase is rendered basic with a 2N sodium hydroxide solution and extracted with ethyl acetate. The combined ethyl acetate phases are dried using brine and magnesium sulfate and evaporated. The title compound is obtained as a yellow resin.

f) Dimethyl N-(7-nitro-2,3-dimethoxyquinoxalin-5-ylmethyl)-α-(ethylamino)ethylphosphonate 300 mg (0.75 mmol) of dimethyl N-(7-nitro-2,3-dimethoxyquinoxalin-5-ylmethyl)-α-aminoethylphosphonate, 0.482 ml (8 eq.) of ethyl iodide and 1.4 ml (11 eq.) of diisopropylethylamine are stirred at 700 for 24 hours in 10 ml of acetonitrile. The reaction mixture is evaporated and the residue is stirred in diethyl ether. The solid is filtered off, washed with diethyl ether and the filtrate is evaporated. The title compound is obtained as a brownish oil.

$^1$H-NMR (CDCl$_3$, 250 MHz); δ=8.63, 8.54 (2d, 2H); 4.37 (s, 2H); 4.19, 4.17 (2s, 2Me); 3.88, 3.73 (2d, 2Me); 3.27 (m, $^1$H); 2.9, 2.7 (2m, 2H); 1.39 (dd, Me); 1.13 (t, Me).

EXAMPLE 5

N-Acetyl-N-(7-nitro-2,3-dioxo-1,2,3,4-tetrahydroquinoxalin-5-ylmethyl) aminoethylphosphonic acid The title compound can be obtained in a manner analogous to that described in Examples 1 and 4, but starting from dimethyl N-(7-nitro-2,3-dimethoxyquinoxalin-5-ylmethyl) aminoethylphosphonate; m.p.=248° C.

EXAMPLE 6

(R)-N-(7-Nitro-2,3-dioxo-1,2,3,4-tetrahydroquinoxalin-5-ylmethyl)-α-(ethylamino) ethylphosphonic acid 4.24 g (9.9 mmol) of dimethyl (R)-N-(7-nitro-2,3-dimethoxyquinoxalin-5-ylmethyl)-α- ethylaminoethylphosphonate are stirred for 19 hours in 80 ml of 6N hydrochloric acid. The reaction mixture is evaporated and the residue is slurried with water. The title compound is obtained as a solid of m.p.=218° C. (dec.).

The starting materials can be prepared, for example, as follows:

a) Dimethyl (R)-N-(7-nitro-2,3-dimethoxyquinoxalin-5-ylmethyl)-α-aminoethylphosphonate 5.14 g (19.5 mmol) of 7-nitro-2,3-dimethoxyquinoxaline-5-carbaldehyde, 3.59 g (1.2 eq.) of L-phosphoalanine dimethyl ester and 18.8 g (8 eq.) of magnesium sulfate are stirred at room temperature for 3 hours in 80 ml of dimethyl sulfoxide. The reaction mixture is filtered off and evaporated. The residue is dissolved in 100 ml of methanol, and treated with 1.12 ml (1 eq.) of acetic acid, 3.2 g (2 eq.) of sodium acetate and 1.71 g (1.4 eq.) of sodium cyanoborohydride. The reaction mixture is stirred at room temperature for 18 hours, treated with 1N hydrochloric acid and extracted with diethyl ether. The aqueous phase is rendered basic using 4N sodium hydroxide solution and extracted with ethyl acetate. The combined organic phases are dried over magnesium sulfate and evaporated. The title compound is obtained as a brown oil;

MS (ES+): 801 (2M+1), 401 (M+1), 291.

b) Dimethyl (R)-N (7-nitro-2,3-dimethoxyquinoxalin-5-ylmethyl)-α-ethylaminoethylphosphonate 3.4 g (8.5 mmol) of dimethyl (R)-N-(7-nitro-2,3-dimethoxyquinoxalin-5-ylmethyl)-α-aminoethylphosphonate, 8.9 ml (7.5 eq.) of ethyl iodide and 20.9 ml (14.5 eq.) of Hünig's base are mixed in 18 ml of acetonitrile and stirred at 55° C. for 18 hours. The reaction mixture is evaporated and slurried with ethyl acetate. The deposited solid is filtered off and washed with ethyl acetate. The title compound is obtained in the form of a yellow resin after evaporation of the filtrate and column chromatography using ethyl acetate/methanol (95:5) as eluent.

NMR (250 MHz,CDCl$_3$); δ(ppm)=8.60, 8.52 (2m, 2H); 4.33 (br.s, 2H); 4.17, 4.16 (2s, 2Me); 3.83, 3.73 (2d, 2MeO); 3.23 (dq, 1H); 2.88, 2.70 (2m, 2H); 1.38 (dd, Me); 1.11 (t, Me).

EXAMPLE 7

(S)-N-(7-Nitro-2,3-dioxo-1,2,3,4-tetrahydroquinoxalin-5-ylmethyl)-α-(ethylamino) ethylphosphonic acid The title compound can be prepared in a manner analogous to that described in Example 6; m.p.=219° C. (dec.).

EXAMPLE 8

(R)-N-(7-Nitro-2,3-dioxo-1,2,3,4-tetrahydroquinoxalin-5-ylmethyl)-α-aminoethylphosphonic acid hydrochloride The title compound can be prepared in a manner analogous to that described in Example 6, but without stage b); m.p.=218° C. (dec.).

EXAMPLE 9

(S)-N-(7-Nitro-2,3-dioxo-1,2,3,4-tetrahydroquinoxalin-5-ylmethyl)-α-aminoethylphosphonic acid hydrochloride The title compound can be prepared in a manner analogous to that described in Example 6, but without stage b); m.p.=218° C. (dec.).

EXAMPLE 10

(R)-N-(7-Bromo-2,3-dioxo-1,2,3,4-tetrahydroquinoxalin-5-ylmethyl)-α-aminoethylphosphonic acid The title compound can be prepared in a manner analogous to that in Example 6, but without stage b), and starting from 5-bromomethyl-7-bromo-2,3-dimethoxyquinoxaline; m.p.=272° C. (dec.).

EXAMPLE 11

(S)-N-(7-Bromo-2,3-dioxo-1,2,3,4-tetrahydroquinoxalin-5-ylmethyl)-α-aminoethylphosphonic acid The title compound can be prepared in a manner analogous to that in Example 6, but without stage b), and starting from 5-bromomethyl-7-bromo-2,3-dimethoxyquinoxaline; m.p.=278° C. (dec.).

EXAMPLE 12

The following can furthermore be prepared in a manner analogous to that described under Examples 3 and 4:

N-(7-chloro-2,3-dioxo-1,2,3,4-tetrahydroquinoxalin-5-ylmethyl)-α-(methylamino)ethylphosphonic acid hydrobromide;

N-(7-fluoro-2,3-dioxo-1,2,3,4-tetrahydroquinoxalin-5-ylmethyl)-α-(ethylamino)ethylphosphonic acid hydrobromide;

N-(7-dioxo-7-nitro-1,2,3,4-tetrahydroquinoxalin-5-ylmethyl)-α-(methylamino)ethylphosphonic acid hydrobromide, m.p.=191° (dec.);

N-(7-dioxo-7-nitro-1,2,3,4-tetrahydroquinoxalin-5-ylmethyl)aminomethylphosphonic acid, m.p.=272° C. (dec.);

N-(2,3-dioxo-7-nitro-1,2,3,4-tetrahydroquinoxalin-5-ylmethyl)-α-(ethylamino)methylphosphonic acid hydrobromide, m.p.=280–285° C. (dec.); and N-(2,3-dioxo-7-nitro-1,2,3,4-tetrahydroquinoxalin-5-ylmethyl)-α-(methylamino)methylphosphonic acid, m.p.>286° C. (dec.).

EXAMPLE 13

N-(2,3-Dioxo-7-nitro-1,2,3,4-tetrahydroquinoxalin-5-ylmethyl)-β-aminopropylphosphonic acid hydrobromide The title compound can be prepared from dimethyl N-(2,3-dimethoxy-7-nitroquinoxalin-5-ylmethyl)-β-aminopropylphosphonate in a manner analogous to that in Example 2 and then recrystallized from dimethylformamide with addition of ethanol and diethyl ether; m.p.=282° C. (dec.).

The starting material can be prepared, for example, in the following manner:

Dimethyl N-(2,3-dimethoxy-7-nitroquinoxalin-5-ylmethyl)-β-aminopropylphosphonate 200 mg (0.757 mmol) of 5-aminomethyl-7-nitro-2,3-dimethoxyquinoxaline, 547 mg (4.5 eq.) of magnesium sulfate and 163 mg (1.3 eq.) of dimethyl 2-oxopropylphosphonate are stirred at room temperature for 20 hours in 8 ml of dichloromethane. 4 ml of methanol, 0.095 ml of acetic acid and 52 mg (1.1 eq.) of sodium cyanoborohydride are then added and stirred for 4 hours.

The reaction mixture is then filtered and the filtrate is extracted with water and brine. The organic phases are combined, dried over magnesium sulfate and evaporated. The title compound is obtained as a brown oil.

EXAMPLE 14

N-(2,3-Dioxo-7-nitro-1,2,3,4-tetrahydroquinoxalin-5-ylmethyl)-2-aminophenylphosphonic acid hydrobromide The title compound can be obtained from diethyl N-(2,3-dimethoxy-7-nitroquinoxalin-5-ylmethyl)-2-aminophenylphosphonate in a manner analogous to that described in Example 4; m.p.=191° (dec.).

The starting material can be prepared, for example, in the following manner:

Diethyl N-(2,3-dimethoxy-7-nitroquinoxalin-5-ylmethyl)-2-aminophenylphosphonate 190 mg (0.579 mmol) of 5-bromomethyl-7-nitro-2,3-dimethoxyquinoxaline, 159 mg (1.2 eq.) of diethyl 2-aminophenylphosphonate and 0.2 ml (2 eq.) of diisopropylethylamine are stirred at reflux for 20 hours in 8 ml of acetonitrile. The reaction mixture is evaporated and the residue is extracted with water and ethyl acetate. The combined organic phases are dried using brine and magnesium sulfate and evaporated. The title compound is obtained as a yellow solid.

$^1$H-NMR (CDCl$_3$, 250 MHz); δ=8.57, 8.29 (2d, 2H); 7.48, 7.25, 6.67, 6.51 (4m, 4H); 4.93 (s, 2H), 4.24, 4.28 (2s, 2Me); 4.10 (m, 2CH$_2$); 1.32 (m, 2CH$_3$).

EXAMPLE 15

The following can furthermore be prepared in a manner analogous to that described under Examples 1 to 4, 13 and 14:

N-(7-bromo-2,3-dioxo-1,2,3,4-tetrahydroquinoxalin-5-ylmethyl)-α-aminobenzylphosphonic acid, m.p.>310°;

N-(7-bromo-2,3-dioxo-1,2,3,4-tetrahydroquinoxalin-5-ylmethyl)-α-amino-3-methylbutylphosphonic acid hydrobromide, m.p.=254–256°;

N-(7-bromo-2,3-dioxo-1,2,3,4-tetrahydroquinoxalin-5-ylmethyl)-α-aminoisobutylphosphonic acid, m.p.=249–251°;

N-(7-bromo-2,3-dioxo-1,2,3,4-tetrahydroquinoxalin-5-ylmethyl)-α-amino-β-benzyloxyethylphosphonic acid, m.p.>280° C., MS (ES-): 484, 482 (M–1);

N-(7-bromo-2,3-dioxo-1,2,3,4-tetrahydroquinoxalin-5-ylmethyl)-α-aminopropylphosphonic acid, m.p.=264–2660;

diethyl N-(2,3-dioxo-7-nitro-1,2,3,4-tetrahydroquinoxalin-5-ylmethyl)-4-aminobenzylphosphonate hydrochloride, MS (ES$^-$): 461 (M-H)$^-$;

N-(2,3-dioxo-7-nitro-1,2,3,4-tetrahydroquinoxalin-5-ylmethyl)-α-amino-(3-hydroxybenzyl)phosphonic acid hydrobromide, m.p.>280°;

N-(2,3-dioxo-7-nitro-1,2,3,4-tetrahydroquinoxalin-5-ylmethyl)-α-amino(isopropyl)phosphonic acid hydrobromide, m.p.=212° (dec.);

N-(2,3-dioxo-7-nitro-1,2,3,4-tetrahydroquinoxalin-5-ylmethyl)-4-aminobenzylphosphonic acid hydrobromide, TLC (t-butylOMe, MeOH, AcOH (80:18:2)); R$_f$=0.27;

trans-2-[N-(2,3-dioxo-7-nitro-1,2,3,4-tetrahydroquinoxalin-5-ylmethyl)amino]cyclopropylphosphonic acid;

N-(2,3-dioxo-7-nitro-1,2,3,4-tetrahydroquinoxalin-5-ylmethyl)-α-methylamino(isopropyl)phosphonic acid hydrobromide, m.p.=212° (dec.);

trans-2-[N-(2,3-dioxo-7-nitro-1,2,3,4-tetrahydroquinoxalin-5-ylmethyl)amino]cyclopropylphosphonic acid hydrobromide, m.p.>320° (dec.);

N-(2,3-dioxo-7-nitro-1,2,3,4-tetrahydroquinoxalin-5-ylmethyl)-α-amino-(3,4,5-trimethoxybenzyl)phosphonic acid hydrobromide, m.p.=265°

N-(2,3-dioxo-7-nitro-1,2,3,4-tetrahydroquinoxalin-5-ylmethyl)-α-aminocyclohexylmethylphosphonic acid hydrobromide, m.p.=255° (dec.);

N-(2,3-dioxo-7-nitro-1,2,3,4-tetrahydroquinoxalin-5-ylmethyl)-α-amino-n-butylphosphonic acid hydrobromide, m.p.=230° (dec.);

N-(2,3-dioxo-7-nitro-1,2,3,4-tetrahydroquinoxalin-5-ylmethyl)-α-amino-3-methylbutylphosphonic acid hydrobromide, m.p.=220° (dec.);

N-(2,3-dioxo-7-nitro-1,2,3,4-tetrahydroquinoxalin-5-ylmethyl)-α-amino-benzylphosphonic acid hydrobromide, m.p.=205° (dec.);

N-(2,3-dioxo-7-nitro-1,2,3,4-tetrahydroquinoxalin-5-ylmethyl)-α-amino-(3-thienyl)methylphosphonic acid hydrobromide, m.p.=205° (dec.);

N-(2,3-dioxo-7-nitro-1,2,3,4-tetrahydroquinoxalin-5-ylmethyl)-(α-amino-(4-methoxycarbonylbenzyl) phosphonic acid hydrobromide, m.p.=270°;

N-(2,3-dioxo-7-nitro-1,2,3,4-tetrahydroquinoxalin-5-ylmethyl)-α-amino-(4-carboxybenzyl)phosphonic acid hydrobromide, m.p.=>280° C.;

N-(2,3-dioxo-7-nitro-1,2,3,4-tetrahydroquinoxalin-5-ylmethyl)-α-amino-(3-nitrobenzyl)phosphonic acid hydrobromide, m.p.=205° (dec.);

N-(2,3-dioxo-7-nitro-1,2,3,4-tetrahydroquinoxalin-5-ylmethyl)-α-amino-(2-hydroxy-3-methoxybenzyl) phosphonic acid hydrobromide, m.p.>330°;

N-(7-chloro-2,3-dioxo-1,2,3,4-tetrahydroquinoxalin-5-ylmethyl)-2-aminophenylphosphonic acid hydrobromide, m.p.>250°;

N-(2,3-dioxo-7-nitro-1,2,3,4-tetrahydroquinoxalin-5-ylmethyl)-α-amino-2-pyrrolylmethylphosphonic acid hydrobromide, m.p.>320°;

N-(2,3-dioxo-7-nitro-1,2,3,4-tetrahydroquinoxalin-5-ylmethyl)-α-amino-(3-methylsulfanylpropyl)phosphonic acid hydrobromide, m.p. 252° C. (dec.);

N-(2,3-dioxo-7-nitro-1,2,3,4-tetrahydroquinoxalin-5-ylmethyl)-α-amino-(2-hydroxy-2-methylpropyl) phosphonic acid hydrobromide, m.p.>256° C.;

N-(7-nitro-2,3-dioxo-1,2,3,4-tetrahydroquinoxalin-5-ylmethyl)-2-aminophenylphosphonic acid hydrobromide;

N-(7-chloro-2,3-dioxo-1,2,3,4-tetrahydroquinoxalin-5-ylmethyl)-α-aminoethylphosphonic acid m.p.>270° C., MS (ES-): 332 (M–1), 250, 207; and N-(7-fluoro-2,3-dioxo-1,2,3,4-tetrahydroquinoxalin-5-ylmethyl)-α-aminoethylphosphonic acid m.p.>250° C., [$^1$H]-NMR (D$_2$O, 250 MHz): δ(ppm)=7.1 (m, 2H); 4.57 (m, 2H); 3.42 (m, 1H); 1.47 (m, 3H).

EXAMPLE 16

P-Benzyl-N-(2,3-dioxo-7-nitro-1,2,3,4-tetrahydroquinoxalin-5-ylmethyl)-aminomethylphosphinic acid hydrobromide The title compound is prepared from diethyl P-benzyl-N-(2,3-dimethoxy-7-nitroquinoxalin-5-ylmethyl) aminomethylphosphinate as described in Example 1; m.p.=196° (dec.).

The starting material can be prepared, for example, as follows:

a) Ethyl P-benzyl-N-(2,3-dimethoxy-7-nitroquinoxalin-5-ylmethyl)aminomethylphosphinate 300 mg (1.136 mmol) of 5-aminomethyl-7-nitro-2,3-dimethoxyquinoxaline, 0.13 ml (2 eq.) of acetaldehyde, 683 mg (5 eq.) of magnesium sulfate and 204 mg (1.3 eq.) of potassium carbonate are stirred at room temperature for 2 hours in 8 ml of dichloromethane. The reaction mixture is filtered off and 0.205 ml (1.3 eq.) of triethylamine, 0.215 ml (1.5 eq.) of trimethylchlorosilane and 209 mg (1 eq.) of ethyl p-benzylphosphinate are added to the filtrate. The reaction mixture is stirred for 18 hours and then extracted with water and dichloromethane. The organic phases are combined, dried over magnesium sulfate and evaporated. The title compound is obtained as a yellow resin; MS(ES+): 353, 537 (M+1)$^+$.

EXAMPLE 17

The following can furthermore be prepared in a manner analogous to that described under Examples 1 and 16:

P-methyl-N-(2,3-dioxo-7-nitro-1,2,3,4-tetrahydroquinoxalin-5-ylmethyl)-α-aminoethylphosphinic acid, m.p. 226° (dec.);

P-benzyl-(7-nitro-2,3-dioxo-1,2,3,4-tetrahydroquinoxalin-5-yl)aminomethanephosphinic acid; and P-methyl-(7-nitro-2,3-dioxo-1,2,3,4-tetrahydroquinoxalin-5-yl)aminomethanephosphinic acid.

EXAMPLE 18

N-(7-Nitro-2,3-dioxo-1,2,3,4-tetrahydroquinoxalin-5-ylmethyl)-4-phosphonobutyramide The title compound can be prepared as under Example 4, but from N-(2,3-dimethoxy-7-nitroquinoxalin-5-ylmethyl)-4-(dimethylphosphono)butyramide; m.p.=220–240° (dec.)

The starting material can be prepared, for example, as follows:

a) N-(2,3-Dimethoxy-7-nitroquinoxalin-5-ylmethyl)-4-(dimethylphosphono)butyramide 163 mg (0.851 mmol) of N-(dimethylaminopropyl)-N'-ethylcarbodiimide hydrochloride are added at room temperature to a solution of 150 mg (0.568 mmol) of 5-aminomethyl-2,3-dimethoxy-7-nitroquinoxaline and 165 mg (0.738 mmol) of 4-(dimethylphosphono)butyric acid in 3 ml of methylene chloride and the mixture is stirred for 30 hours. The mixture is then diluted with methylene chloride and washed with 0.2N hydrochloric acid and brine and concentrated on a rotary evaporator, and the residue is dried in a high vacuum. The title compound is obtained as a yellow resin.

EXAMPLE 19

The following can furthermore be prepared in a manner analogous to that described under Example 18:

N-(7-nitro-2,3-dioxo-1,2,3,4-tetrahydroquinoxalin-5-ylmethyl)-2-phosphonoacetamide, m.p.=280–283° (dec.);

N-(7-nitro-2,3-dioxo-1,2,3,4-tetrahydroquinoxalin-5-ylmethyl)-3-phosphonopropenic acid amide, m.p. 240–260° (dec.); and N-(7-nitro-2,3-dioxo-1,2,3,4-tetrahydroquinoxalin-5-ylmethyl)-2-phosphonoindan-2-carboxamide, m.p. 280–2900 (dec.).

EXAMPLE 20

N-Benzyl-N-(2,3-dioxo-7-nitro-1,2,3,4-tetrahydroquinoxalin-5-ylmethyl) aminomethylphosphonic acid hydrobromide 0.7 g (1.4 mmol) of diethyl N-benzyl-N-(2,3-dimethoxy-7-nitroquinoxalin-5-ylmethyl)-α-methylphosphonate and 1.1 ml (8.3 mmol) of trimethylsilyl bromide are stirred at room temperature for 16 hours in 7 ml of methylene chloride. 7 ml of ethanol are then added and stirred at room temperature for a further 24 hours. The reaction mixture is evaporated, the residue is dissolved in 7 ml of acetic acid, 7 ml of 33% HBr in acetic acid are added and the mixture is stirred at room temperature for 4 hours. After addition of 60 ml of ether, a suspension is formed, which is filtered off on a suction filter. The suction filter material is washed with ether and dried at 60° in vacuo. The crystals are then stirred in ethyl acetate and filtered off again. The title compound is obtained as grayish crystals of m.p. 238–240° (decomposition).

The starting material can be prepared, for example, as follows:

a) Diethyl N-benzyl-N-(2,3-dimethoxy-7-nitro-quinoxalin-5-ylmethyl)aminomethylphosphonate 1.0 g (3.05 mmol) of 5-bromomethyl-2,3-dimethoxy-7-nitroquinoxaline, 1.1 g (3.66 mmol) of diethyl benzylaminomethanephosphonate hydrochloride and 1.9 ml (10.98 mmol) of N-ethyldiisopropylamine are stirred at room temperature for about 18 hours and at 80° C. for a further 3 hours in 10 ml of dimethylformamide under argon. After addition of ethyl acetate, the mixture is extracted with water and brine, the aqueous phases are washed with ethyl acetate, and the organic phases are combined, dried using sodium sulfate, filtered on a suction filter and concentrated. The evaporation residue is chromatographed on silica gel using hexane-ethyl acetate (1:1). 0.71 g (46%) of diethyl N-benzyl-N-(2,3-dimethoxy-7-nitroquinoxalin-5-ylmethyl) aminomethylphosphonate is obtained.

EXAMPLE 21

The following compounds are also prepared in a manner analogous to that described in Example 20:

N-benzyl-N-(7-bromo-2,3-dioxo-1,2,3,4-tetrahydroquinoxalin-5-ylmethyl) aminomethylphosphonic acid;

N-benzyl-N-(7-chloro-2,3-dioxo-1,2,3,4-tetrahydroquinoxalin-5-ylmethyl) aminomethylphosphonic acid, m.p. 245–248° (dec.); and N-benzyl-N-(2,3-dioxo-7-fluoro-1,2,3,4-tetrahydroquinoxalin-5-ylmethyl) aminomethylphosphonic acid.

EXAMPLE 22

N-Benzyl-N-(2,3-dioxo-7-nitro-1,2,3,4-tetrahydroquinoxalin-5-ylmethyl)-α-aminoethanephosphonic acid The title compound, m.p. 254–257° (dec.), can be obtained starting from 5-bromomethyl-2,3-dimethoxy-7-nitroquinoxaline and diethyl 2-benzylaminoethanephosphonate in a manner analogous to that described in Example 1.

EXAMPLE 23

N-(2,3-Dioxo-7-fluoro-1,2,3,4-tetrahydroquinoxalin-5-ylmethyl)-α-aminoethylphosphonic acid The title compound can be obtained by solvolysis of dimethyl N-(2,3-dimethoxy-7-fluoroquinoxalin-5-ylmethyl)-α-aminoethylphosphonate in a manner analogous to that described in Example 1. The starting material (dimethyl N-(2,3-dimethoxy-7-fluoroquinoxalin-5-ylmethyl)-α-aminoethylphosphonate) can be prepared in a manner analogous to that described in Example 4, e1):

¹H-NMR (CDCl₃, 300 MHz); δ=7.2–7.4 (2H), 4.2-4.4 (2H), 4.12 (s, 6H), 3.0 (m, 1H), 1.28–1.45 (m, 3H).

EXAMPLE 24

The following compounds are also prepared in a manner analogous to that described in Examples 1 to 23:

(R)-N-(7-nitro-2,3-dioxo-1,2,3,4-tetrahydroquinoxalin-5-ylmethyl)-β-aminopropylphosphonic acid hydrochloride, m.p.=293° C. (dec);

(S)-N-(7-nitro-2,3-dioxo-1,2,3,4-tetrahydroquinoxalin-5-ylmethyl)-β-aminopropylphosphonic acid hydrochloride, m.p.=295° (dec);

N-(2,3-dioxo-7-nitro-1,2,3,4-tetrahydroquinoxalin-5-ylmethyl)-α-aminopropylphosphonic acid hydrochloride, m.p.=2350 (dec.);

N-(2,3-dioxo-7-nitro-1,2,3,4-tetrahydroquinoxalin-5-ylmethyl)-α-amino(tetrahydropyran-4-yl)phosphonic acid hydrochloride, m.p.=310° C. (dec.);

N-(2,3-dioxo-7-nitro-1,2,3,4-tetrahydroquinoxalin-5-ylmethyl)-α-amino(piperidin-4-yl)phosphonic acid dihydrochloride, m.p.=251° C. (dec.);

N-(2,3-dioxo-7-nitro-1,2,3,4-tetrahydroquinoxalin-5-ylmethyl)-α-amino(furan-2-ylmethyl)phosphonic acid hydrochloride;

N-(2,3-dioxo-7-nitro-1,2,3,4-tetrahydroquinoxalin-5-ylmethyl)-α-amino-(2-methoxy)ethylphosphonic acid hydrochloride;

N-(2,3-dioxo-7-nitro-1,2,3,4-tetrahydroquinoxalin-5-ylmethyl)-2-amino-2-cyclohexylethylphosphonic acid hydrochloride;

N-(2,3-dioxo-7-nitro-1,2,3,4-tetrahydroquinoxalin-5-ylmethyl)-β-aminoisopropylphosphonic acid hydrochloride;

N-(2,3-dioxo-7-nitro-1,2,3,4-tetrahydroquinoxalin-5-ylmethyl)-2-aminocyclohexylphosphonic acid hydrochloride;

N-(2,3-dioxo-7-nitro-1,2,3,4-tetrahydroquinoxalin-5-ylmethyl)-2-amino-2-methylpropylphosphonic acid hydrochloride;

N-(2,3-dioxo-7-nitro-1,2,3,4-tetrahydroquinoxalin-5-ylmethyl)-2-aminobutylphosphonic acid hydrochloride;

N-(2,3-dioxo-7-nitro-1,2,3,4-tetrahydroquinoxalin-5-ylmethyl)-2-aminoheptylphosphonic acid hydrochloride, MS(FB+): 415 (M+1);

N-(2,3-dioxo-7-nitro-1,2,3,4-tetrahydroquinoxalin-5-ylmethyl)-2-amino-3-phenoxypropylphosphonic acid hydrochloride, m.p.=234° C. (dec.);

N-(2,3-dioxo-7-nitro-1,2,3,4-tetrahydroquinoxalin-5-ylmethyl)-2-ethylaminoethylphosphonic acid, m.p.=286° C. (dec.);

N-(2,3-dioxo-7-nitro-1,2,3,4-tetrahydroquinoxalin-5-ylmethyl)-2-benzylaminoethylphosphonic acid, m.p.=225° C. (dec.);

N-(2,3-dioxo-7-nitro-1,2,3,4-tetrahydroquinoxalin-5-ylmethyl)-2-amino-2-p-tolylethylphosphonic acid hydrochloride;

N-(2,3-dioxo-7-nitro-1,2,3,4-tetrahydroquinoxalin-5-ylmethyl)-2-amino-2-(2-methoxyphenyl)ethylphosphonic acid hydrochloride;

N-(2,3-dioxo-7-nitro-1,2,3,4-tetrahydroquinoxalin-5-ylmethyl)-2-amino-2-(4-fluorophenyl)ethylphosphonic acid hydrochloride;

N-(2,3-dioxo-7-nitro-1,2,3,4-tetrahydroquinoxalin-5-ylmethyl)-2-amino-2-phenylethylphosphonic acid hydrochloride, m.p.=258° C. (dec.);

P-methyl-N-(2,3-dioxo-7-nitro-1,2,3,4-tetrahydroquinoxalin-5-ylmethyl)-2-amino-2-phenylethylphosphinic acid hydrochloride, m.p.=258° C. (dec.);

N-(2,3-dioxo-7-nitro-1,2,3,4-tetrahydroquinoxalin-5-ylmethyl)-2-amino-1-phenylethylphosphonic acid hydrochloride, m.p.=262° C. (dec.);

N-(2,3-dioxo-7-nitro-1,2,3,4-tetrahydroquinoxalin-5-ylmethyl)-2-amino-1-(furan-2-yl)ethylphosphonic acid hydrochloride;

N-(2,3-dioxo-7-nitro-1,2,3,4-tetrahydroquinoxalin-5-ylmethyl)-2-amino-1-(4-fluorophenyl)ethylphosphonic acid hydrochloride;

N-(2,3-dioxo-7-nitro-1,2,3,4-tetrahydroquinoxalin-5-ylmethyl)-2-amino-1-(4-methoxyphenyl)ethylphosphonic acid hydrochloride;

N-(2,3-dioxo-7-nitro-1,2,3,4-tetrahydroquinoxalin-5-ylmethyl)-2-amino-1-(3-methoxyphenyl)ethylphosphonic acid hydrochloride;

N-(2,3-dioxo-7-nitro-1,2,3,4-tetrahydroquinoxalin-5-ylmethyl)-2-amino-1-(2-chlorophenyl)ethylphosphonic acid hydrochloride;

N-(2,3-dioxo-7-nitro-1,2,3,4-tetrahydroquinoxalin-5-ylmethyl)-2-amino-1-(4-tolyl)ethylphosphonic acid hydrochloride;

N-benzyl-N-(7-bromo-2,3-dioxo-1,2,3,4-tetrahydroquinoxalin-5-ylmethyl)-α-aminoethylphosphonic acid;

{1-[(7-bromo-2,3-dioxo-1,2,3,4-tetrahydroquinoxalin-5-ylmethyl)amino]cyclopropyl}phosphonic acid, m.p.= 295° C. (dec);

N-benzyl-N-(7-chloro-2,3-dioxo-1,2,3,4-tetrahydroquinoxalin-5-ylmethyl)-α-aminoethylphosphonic acid; and N-benzyl-N-(2,3-dioxo-7-fluoro-1,2,3,4-tetrahydroquinoxalin-5-ylmethyl)-α-aminoethylphosphonic acid.

EXAMPLE 25

Starting from 7-cyano-5-methyl-2,3-dimethoxyquinoxaline, the following compounds can also be prepared in a manner analogous to that described in Examples 1 to 23:

N-(7-cyano-2,3-dioxo-1,2,3,4-tetrahydroquinoxalin-5-ylmethyl)-α-aminoethylphosphonic acid, m.p.>270° C., H-NMR (DMSO, 250 MHz): δ=(ppm)= 7.62, 7.47 (2m, 2H); 4.50, 4.40 (2d, 2H); 3.22 (m,1 H); 1.36 (q, Me); and N-(7-cyano-2,3-dioxo-1,2,3,4-tetrahydroquinoxalin-5-ylmethyl)-α-ethylaminoethylphosphonic acid hydrochloride, m.p.>270° C., MS(ES+): 353 (M+1).

The starting material can be obtained, for example, in the following manner:

a) 7-Cyano-5-methyl-2,3-dimethoxyguinoxaline

A solution of 7 g (24.72 mmol) of 7-bromo-5-methyl-2,3-dimethoxyquinoxaline (Example 1d), 1.74 g of zinc cyanide (14.83 mmol) and 1.1 g (0.9 mmol) of tetrakis (triphenylphosphine)palladium(0) are dissolved in 100 ml of DMF, degassed and brought under a nitrogen atmosphere. The mixture is then heated at 80° C. for 16 hours. After cooling, the reaction mixture is treated with 2N hydrochloric acid and extracted with ethyl acetate. The combined organic phases are washed with brine, dried over sodium sulfate and evaporated. The residue is chromatographed on silica gel using ethyl acetate/hexane (9:1-1:1) as eluent; m.p. 179–180° C. (ethyl acetate/hexane);

¹H-NMR (250 MHz, CDCl₃): δ=7.94 (d, J=3, 1H), 7.51 (d, J=3, 1H), 4.18 (s, 3H), 4.16 (s, 3H), 2.64 (s, 3H); MS(ES+): 230

EXAMPLE 26

Starting from 7-trifluoromethyl-5-methyl-1,4-dihydroquinoxaline-2,3-dione, the following compounds can also be prepared in a manner analogous to that described in Examples 1 to 23:

(R)-N-(7-trifluoro-2,3-dioxo-1,2,3,4-tetrahydroquinoxalin-5-ylmethyl)-α-aminoethylphosphonic acid, $[\alpha]_D=-19.6°$ (c=1, MeOH);

(S)-N-(7-trifluoromethyl-2,3-dioxo-1,2,3,4-tetrahydroquinoxalin-5-ylmethyl)-α-aminoethylphosphonic acid, $[\alpha]_D=+17.7°$ (c=1, MeOH);

(R)-N-(7-trifluoromethyl-2,3-dioxo-1,2,3,4-tetrahydroquinoxalin-5-ylmethyl)-α-(ethylamino) ethylphosphonic acid, $[\alpha]_D=+74°$ (c=0.1, H$_2$O), m.p.>270° C.;

N-(7-trifluoromethyl-2,3-dioxo-1,2,3,4-tetrahydroquinoxalin-5-ylmethyl)-β-(ethylamino) ethylphosphonic acid, m.p.=230° C. (dec.);

(S)-N-(7-trifluoromethyl-2,3-dioxo-1,2,3,4-tetrahydroquinoxalin-5-ylmethyl)-α-(ethylamino) ethylphosphonic acid, $[\alpha]_D=-78°$ (c=0.1, H$_2$O), m.p.>270° C., MS(ES-): 394 (M−1);

(R)-N-(7-trifluoromethyl-2,3-dioxo-1,2,3,4-tetrahydroquinoxalin-5-ylmethyl)-β-aminopropylphosphonic acid hydrochloride, m.p.=282° C. (dec.);

(S)-N-(7-trifluoromethyl-2,3-dioxo-1,2,3,4-tetrahydroquinoxalin-5-ylmethyl)-β-aminopropylphosphonic acid hydrochloride, m.p.=281° C. (dec.); and N-(7-trifluoromethyl-2,3-dioxo-1,2,3,4-tetrahydroquinoxalin-5-ylmethyl) aminomethylphosphonic acid, m.p.=321–323° C. (dec.).

The starting material can be prepared, for example, in the following manner:

a) Ethyl N-(2-methyl-4-trifluoromethylphenyl)oxamate

A solution of 37.5 g (214 mmol) of 2-methyl-4-trifluoromethylaniline (DE 2750170 A1) and 44.7 ml (321 mmol) of triethylamine in 750 ml of ethyl acetate is cooled to +3° C. by means of an icebath. Ethyl oxalyl chloride (26.2 ml, 235.5 mmol) is slowly added dropwise so that the temperature does not rise above +10° C. The mixture is then stirred for a further 2 hours. The mixture is treated with water, washed with a 10% aqueous sodium hydrogencarbonate solution and with brine, dried over sodium sulfate and concentrated. Crystallization of the crude product affords 52.75 g of the title compound as white crystals.

M.p. 120–121° C. (ethyl acetate/hexane)

$^1$H-NMR (300 MHz, CDCl$_3$): δ=8.98 (br s, 1H), 8.29 (d, J=8, 1H), 7.53 (d, J=8, 1H), 7.49 (s, 1H), 4.45 (q, J=7, 2H), 2.40 (s, 3H), 1.64 (t, J=7, 3H).

b) Ethyl N-(2-methyl-6-nitro-4-trifluoromethylphenyl) oxamate 14.4 g (142.3 mmol) of potassium nitrate are added in small portions to an ice-cooled solution of 32.6 g (118.6 mmol) of ethyl N-(2-methyl-4-trifluoromethylphenyl) oxamate in concentrated sulfuric acid. After stirring at 0° C. for 1.5 hours, the mixture is cautiously poured onto 900 g of ice. The white suspension is extracted with ethyl acetate. The organic phase is washed with brine, dried over sodium sulfate and concentrated under reduced pressure in a rotary evaporator. Crystallization from ethyl acetate/hexane affords 35.5 g of the title compound as white crystals.

M.p.: 118–120° C.

$^1$H-NMR (200 MHz, CDCl$_3$): δ=9.94 (br s, NH), 8.17 (s, 1H), 7.81 (s, 1H), 4.45 (q, J=7, 2H), 2.41 (s, 3H), 1.43 (t, J=7, 3H).

c) 7-Trifluoromethyl-5-methyl-1,4-dihydroquinoxaline-2,3-dione 355 ml of a 15% titanium trichloride solution in aqueous hydrochloric acid are dissolved in 850 ml of water and 850 ml of acetone under a nitrogen atmosphere at 0° C. A solution of 35.5 g (110.8 mmol) of ethyl N-(2-methyl-6-nitro-4-trifluoromethylphenyl)oxamate in 1.7 l of acetone is slowly added dropwise. The resulting violet solution is stirred at 0° C. for 16 hours. 15% titanium trichloride solution in aqueous hydrochloric acid is then added until, according to $^1$H-NMR analysis, starting material is no longer detectable. The reaction mixture is filtered off on a suction filter, the filtrate is concentrated and the deposited solid is filtered off again on a suction filter. The crude product is washed with dilute hydrochloric acid and water. The title compound is obtained as a white solid.

MS(ES$^+$): 245 (M+H)$^+$ $^1$H-NMR (200 MHz, DMSO-d$_6$): δ=12.1 (s, NH), 11.5 (s, NH), 7.30 (s, 1H), 7.28 (s, 1H), 2.40 (s, 3H).

EXAMPLE 27

Tablets each comprising 50 mg of N-(2,3-dioxo-7-nitro-1,2,3,4-tetrahydroquinoxalin-5-ylmethyl)-α-amino (isopropyl)phosphonic acid or a salt, e.g. the hydrobromide, thereof can be prepared as follows:

| Composition (10,000 tablets) | |
| --- | --- |
| Active ingredient | 500.0 g |
| Lactose | 500.0 g |
| Potato starch | 352.0 g |
| Gelatin | 8.0 g |
| Talc | 60.0 g |
| Magnesium stearate | 10.0 g |
| Silica (highly disperse) | 20.0 g |
| Ethanol | q.s. |

The active ingredient is mixed with the lactose and 292 g of potato starch, and the mixture is moistened with an ethanolic solution of the gelatin and granulated through a sieve. After drying, the remainder of the potato starch, the magnesium stearate, the talc and the silica are admixed and the mixture is compressed to give tablets of weight 145.0 mg each and 50.0 mg active ingredient content, which, if desired, can be provided with breaking notches for finer adjustment of the dose.

EXAMPLE 28

A sterile-filtered aqueous gelatin solution with 20% cyclodextrins as solubilizer, comprising 3 mg of N-(2,3-dioxo-7-nitro-1,2,3,4-tetrahydroquinoxalin-5-ylmethyl)-α-amino (isopropyl)phosphonic acid each or a salt, e.g. the hydrobromide, thereof as active ingredient is mixed with warming with a sterile gelatin solution, which as preservative contains phenol, under aseptic conditions such that 1.0 ml of solution has the following composition:

| | |
| --- | --- |
| Active ingredient | 3 mg |
| Gelatin | 150.0 mg |
| Phenol | 4.7 mg |
| Dist. water with 20% cyclodextrins as solubilizer | 1.0 ml |

EXAMPLE 29

For the preparation of a sterile dry substance for injection, comprising 5 mg each of N-(2,3-dioxo-7-nitro-1,2,3,4-tetrahydroquinoxalin-5-ylmethyl)-α-amino(isopropyl) phosphonic acid or a salt, e.g. the hydrobromide, thereof 5 mg of one of the compounds of the formula I mentioned in the preceding examples is dissolved as active ingredient in 1 ml of an aqueous solution with 20 mg of mannitol and 20% cyclodextrins as solubilizer. The solution is sterile-filtered and filled under aseptic conditions into a 2 ml ampoule, intensely cooled and lyophilized. Before use, the lyophilisate is dissolved in 1 ml of distilled water or 1 ml of physiological saline solution. The solution is administered intramuscularly or intravenously. This formulation can also be dispensed in double-chamber injection ampoules.

EXAMPLE 30

10,000 lacquered tablets, comprising 100 mg each of N-(2,3-dioxo-7-nitro-1,2,3,4-tetrahydroquinoxalin-5-ylmethyl)-α-amino(isopropyl)phosphonic acid or a salt, e.g. the hydrobromide, thereof, can be prepared as follows:

| | |
|---|---|
| Active ingredient | 1000 g |
| Cornstarch | 680 g |
| Colloidal silicic acid | 200 g |
| Magnesium stearate | 20 g |
| Stearic acid | 50 g |
| Sodium carboxymethylstarch | 250 g |
| Water | q.s. |

A mixture of one of the compounds of the formula I mentioned in the preceding examples as active ingredient, 50 g of cornstarch and the colloidal silicic acid is processed with a starch paste from 250 g of cornstarch and 2.2 kg of demineralized water to give a moist mass. This is forced through a sieve of 3 mm mesh width and dried at 45° C. for 30 minutes in a fluidized bed dryer. The dried granules are pressed through a sieve of 1 mm mesh width, mixed with a previously sieved mixture (1 mm sieve) of 330 g of cornstarch, magnesium stearate, stearic acid and sodium carboxymethylstarch and compressed to give slightly curved tablets.

EXAMPLE 31

In a manner analogous to that described in Examples 27 to 30, further pharmaceutical preparations comprising another compound according to one of Examples 1 to 26 can be prepared.

What is claimed is:

1. A compound of the formula I

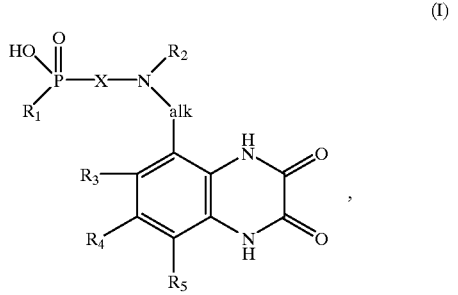

(I)

in which $R_1$ is hydroxyl or an aliphatic, araliphatic or aromatic radical,

X is a divalent aliphatic, cycloaliphatic, cycloaliphatic-aliphatic, araliphatic, heteroarylaliphatic or aromatic radical, $R_2$ is hydrogen or an aliphatic or araliphatic radical, alk is lower alkylidene and $R_3$, $R_4$ and $R_5$ independently of one another are hydrogen, lower alkyl, halogen, trifluoromethyl, cyano or nitro, with the proviso that a1) $R_4$ is other than nitro when X is methylene, 3-hydroxybenzylidene, 3-methoxybenzylidene, 3-pyridylmethylene, ethylene, oxoethylene, ethylidene, 1,3-propylene, 1,3-(1-carboxy) propylene, cyclopropylene or 1,4-butylene, $R_1$ is hydroxyl, alk is methylene and $R_2$, $R_3$ and $R_5$ are hydrogen, or when X is methylene, $R_1$ is methyl or benzyl, alk is methylene and $R_2$, $R_3$ and $R_5$ are hydrogen, or when X is butylene, $R_1$ is hydroxyl, alk is methylene, $R_2$ is methyl and $R_3$ and $R_5$ are hydrogen and b1) $R_4$ is other than bromine when X is methylene or ethylidene, $R_1$ is hydroxyl, alk is methylene and $R_2$, $R_3$ and $R_5$ are hydrogen, or a salt thereof.

2. A compound according to claim 1, in which $R_1$ is hydroxyl, lower alkyl, lower alkenyl, phenyl-lower alkyl, naphthyl-lower alkyl, phenyl or naphthyl, X is lower alkylene, lower alkylidene, oxo-lower alkylene, oxo-lower alkenylene, polyhalo-lower alkylidene, carboxy-lower alkylidene, hydroxy-lower alkylidene, lower alkoxy-lower alkylidene, lower alkylthio-lower alkylidene, 3- to 6-membered cycloalkylene, 3- to 6-membered cycloalkylidene, 3- to 6-membered benzocycloalkenylidene, 3- to 6-membered cycloalkyl-lower alkylene, 3- to 6-membered cycloalkyl-lower alkylidene, phenyl-lower alkylene, phenyl(oxo)-lower alkylene, phenyl-lower alkylidene, pyrrolyl-lower alkylidene, furyl-lower alkylidene, thienyl-lower alkylidene, pyridyl-lower alkylidene, phenylene or naphthylene, $R_2$ is hydrogen, lower alkyl, lower alkenyl, phenyl-lower alkyl or naphthyl-lower alkyl, where the ring system of the cycloalkylene, cycloalkylidene, unfused or benzo-fused cycloalkylene, cycloalkylidene or cycloalkenylidene, cycloalkyl-lower alkylidene, cycloalkyl-lower alkenylidene, phenyl-lower alkylene, phenyl(oxo)-lower alkylene, phenyl-lower alkylidene, furyl-lower alkylidene, thienyl-lower alkylidene, pyridyl-lower alkylidene, phenylene, naphthylene, phenyl-lower alkyl and naphthyl-lower alkyl radicals mentioned can be substituted by lower alkyl, lower alkoxy, phenoxy, hydroxyl, halogen, trifluoromethyl, di-lower alkylamino, lower alkanoylamino, nitro, carboxyl, lower alkoxycarbonyl, carbamoyl and/or cyano, alk is lower alkylidene and $R_3$, $R_4$ and $R_5$ independently of one another are hydrogen, lower alkyl, halogen, trifluoromethyl, cyano or nitro, or a salt thereof.

3. A compound according to claim 1, in which $R_1$ is hydroxyl, $C_1$–$C_4$alkyl, phenyl-$C_1$–$C_4$alkyl, or phenyl, X is straight-chain or branched $C_1$–$C_4$alkylene, straight-chain or branched $C_1$–$C_4$alkylidene, oxo-$C_2$–$C_4$alkylene, oxo-$C_3$–$C_4$alkenylene, straight-chain or branched $C_1$–$C_4$alkylene, polyhalo-$C_1$–$C_4$alkylidene, carboxy-$C_1$–$C_4$alkylidene, hydroxy-$C_2$–$C_4$alkylidene, 3- to 6-membered cycloalkylene, 3- to 6-membered cycloalkylidene, 3- to 6-membered benzocycloalkenylidene, a phenyl(oxo)-$C_2$–$C_4$alkylene radical, or phenyl-$C_1$–$C_4$alkylidene radical which is unsubstituted or substituted by $C_1$–$C_4$alkyl, $C_1$–$C_4$alkoxy, phenoxy, hydroxyl, halogen of atomic number up to and including 35, trifluoromethyl, di-$C_1$–$C_4$alkylamino, $C_1$–$C_7$alkanoylamino, nitro, carboxyl, $C_1$–$C_4$alkoxycarbonyl, carbamoyl and/or cyano; pyrrolyl-$C_1$–$C_4$alkylidene, furyl-$C_1$–$C_4$alkylidene thienyl-$C_1$–$C_4$alkylidene, or phenylene, $R_2$ is hydrogen, $C_1$–$C_4$alkyl, phenyl-$C_1$–$C_4$alkyl which is unsubstituted or substituted by $C_1$–$C_4$alkyl, $C_1$–$C_4$alkoxy, hydroxyl, halogen of atomic number up to and including 35, trifluoromethyl, nitro, carboxyl, $C_1$–$C_4$alkoxycarbonyl, carbamoyl and/or cyano, alk is $C_1$–$C_4$alkylidene, and $R_3$, $R_4$ and $R_5$ independently of one another are hydrogen, $C_1$–$C_4$alkyl, halogen of atomic number up to and including 35, trifluoromethyl, cyano or nitro, or a salt thereof.

4. A compound according to claim 1, in which $R_1$ is hydroxyl, straight-chain or branched $C_1$–$C_4$alkylidene, straight-chain or branched $C_1$–$C_4$alkylene, oxo-$C_2$–$C_4$alkylene, 3- to 6-membered cycloalkylene, or 3- to 6-membered cycloalkylidene, $R_2$ is hydrogen or $C_1$–$C_4$alkyl, alk is $C_1$–$C_4$alkylidene, and $R_3$, $R_4$ and $R_5$ independently of one another are hydrogen, $C_1$–$C_4$alkyl, or halogen of atomic number up to and including 35, trifluoromethyl, cyano or nitro, or a salt thereof.

5. A compound according to claim 1, in which $R_1$ is hydroxyl, straight-chain or branched $C_1$–$C_4$alkylidene, straight-chain or branched $C_1$–$C_4$alkylene, 3- to 6-membered cycloalkylene, or 3- to 6-membered cycloalkylidene, $R_2$ is hydrogen or $C_1$–$C_4$alkyl, alk is $C_1$–$C_4$-alkylidene, $R_4$ is hydrogen, $C_1$–$C_4$alkyl, halogen of atomic number up to and including 35, trifluoromethyl, cyano or nitro, and $R_3$ and $R_5$ are hydrogen, or a salt thereof.

6. A compound according to claim 1, selected from

N-acetyl-N-(7-bromo-2,3-dioxo- 1,2,3,4-tetrahydroquinoxalin-5-ylmethyl) aminomethylphosphonic acid;

N-acetyl-N-(7-chloro-2,3-dioxo-1,2,3,4-tetrahydroquinoxalin-5-ylmethyl) aminomethylphosphonic acid;

N-acetyl-N-(7-fluoro-2,3-dioxo-1,2,3,4-tetrahydroquinoxalin-5-ylmethyl) aminomethylphosphonic acid;

N-(2, 3-dioxo-7-nitro-1,2,3,4-tetrahydroquinoxalin-5-ylmethyl)-α-(ethylamino)ethylphosphonic acid;

N-acetyl-N-(7-nitro-2,3-dioxo- 1,2,3,4-tetrahydroquinoxalin-5-ylmethyl)aminoethylphosphonic acid;

(R)-N-(7-nitro-2,3-dioxo-1,2,3,4-tetrahydroquinoxalin-5-ylmethyl)-α-(ethylamino)ethylphosphonic acid;

(S)-N-(7-nitro-2,3-dioxo- 1,2,3,4-tetrahydroquinoxalin-5-ylmethyl)-α-(ethylamino)ethylphosphonic acid;

(R)-N-(7-nitro-2,3-dioxo-1,2,3,4-tetrahydroquinoxalin-5-ylmethyl)-α-aminoethylphosphonic acid;

(S)-N-(7-nitro-2,3-dioxo-1,2, 3,4-tetrahydroquinoxalin-5-ylmethyl)-α-aminoethylphosphonic acid;

(R)-N-(7-bromo-2,3-dioxo-1,2,3,4-tetrahydroquinoxalin-5-ylmethyl)-α-aminoethylphosphonic acid;

(S)-N-(7-bromo-2,3-dioxo-1,2,3,4-tetrahydroquinoxalin-5-ylmethyl)-α-aminoethylphosphonic acid;

N-(7-chloro-2,3-dioxo-1,2,3,4-tetrahydroquinoxalin-5-ylmethyl)-α-(methylamino)ethylphosphonic acid;

N-(7-fluoro-2,3-dioxo-1,2,3,4-tetrahydroquinoxalin-5-ylmethyl)-α(ethylamino)ethylphosphonic acid;

N-(2,3-dioxo-7-nitro-1,2,3,4-tetrahydroquinoxalin-5-ylmethyl)-α-(methylamino)ethylphosphonic acid;

N-(2,3-dioxo-7-nitro-1,2,3,4-tetrahydroquinoxalin-5-ylmethyl)aminomethylphosphonic acid;

N-(2,3-dioxo-7-nitro-1,2,3,4-tetrahydroquinoxalin-5-ylmethyl)-α-(ethylamino)methylphosphonic acid;

N-(2,3-dioxo-7-nitro-1,2,3,4-tetrahydroquinoxalin-5-ylmethyl)-α-(methylamino)methylphosphonic acid;

N-(2,3-dioxo-7-nitro-1,2,3,4-tetrahydroquinoxalin-5-ylmethyl)-β-aminopropylphosphonic acid;

N-(2,3-dioxo-7-nitro-1,2,3,4-tetrahydroquinoxalin-5-ylmethyl)-2-aminophenylphosphonic acid;

N-(7-bromo-2,3-dioxo- 1,2,3,4-tetrahydroquinoxalin-5-ylmethyl)-α-aminobenzylphosphonic acid;

N-(7-bromo-2,3-dioxo-1,2,3,4-tetrahydroquinoxalin-5-ylmethyl)-α-amino-3-methylbutylphosphonic acid;

N-(7-bromo-2,3-dioxo-1,2,3,4-tetrahydroquinoxalin-5-ylmethyl)-α-amino-β-benzyloxyethylphosphonic acid;

N-(7-bromo-2,3-dioxo-1,2,3,4-tetrahydroquinoxalin-5-ylmethyl)-α-aminoisobutylphosphonic acid;

N-(7-bromo-2,3-dioxo-1,2,3,4-tetrahydroquinoxalin-5-ylmethyl)-α-aminopropylphosphonic acid;

diethyl N-(2,3-dioxo-7-nitro-1,2,3,4-tetrahydroquinoxalin-5-ylmethyl)-4-aminobenzylphosphonate;

N-(2,3-dioxo-7-nitro-1,2,3,4-tetrahydroquinoxalin-5-ylmethyl)-α-amino-(3-hydroxybenzyl)phosphonic acid;

N-(2,3-dioxo-7-nitro-1,2,3,4-tetrahydroquinoxalin-5-ylmethyl)-α-amino(isopropy)phosphonic acid;

N-(2,3-dioxo-7-nitro-1,2,3,4-tetrahydroquinoxalin-5-ylmethyl)-4-aminobenzylphosphonic acid;

trans-2-[N-(2,3-dioxo-7-nitro-1,2,3,4-tetrahydroquinoxalin-5-ylmethyl)amino] cyclopropylphosphonic acid;

N-(2,3-dioxo-7-nitro-1,2,3,4-tetrahydroquinoxalin-5-ylmethyl)-α-methylamino(isopropyl)phosphonic acid;

trans-2-[N-(2,3-dioxo-7-nitro-1,2,3,4-tetrahydroquinoxalin-5-ylmethyl)amino]cyclopropylphosphonic acid;

N-(2,3-dioxo-7-nitro-1,2,3,4-tetrahydroquinoxalin-5-ylmethyl)-α-amino-(3,4,5-trimethoxybenzyl)phosphonic acid;

N-(2,3-dioxo-7-nitro-1,2,3,4-tetrahydroquinoxalin-5-ylmethyl)-α-aminocyclohexylmethylphosphonic acid;

N-(2,3-dioxo-7-nitro-1,2,3,4-tetrahydroquinoxalin-5-ylmethyl)-α-amino-n-butylphosphonic acid;

N-(2,3-dioxo-7-nitro- 1,2,3,4-tetrahydroquinoxalin-5-ylmethyl)-α-amino-3-methylbutylphosphonic acid;

N-(2,3-dioxo-7-nitro-1,2,3,4-tetrahydroquinoxalin-5-ylmethyl)-α-aminobenzylphosphonic acid;

N-(2,3-dioxo-7-nitro-1,2,3,4-tetrahydroquinoxalin-5-ylmethyl)-α-amino-(3-thienyl)methylphosphonic acid;

N-(2,3-dioxo-7-nitro-1,2,3,4-tetrahydroquinoxalin-5-ylmethyl)-α-amino-(4-methoxycarbonylbenzyl) phosphonic acid;

N-(2,3-dioxo-7-nitro-1,2,3,4-tetrahydroquinoxalin-5-ylmethyl)-α-amino(4-carboxybenzyl)phosphonic acid;

N-(2,3-dioxo-7-nitro-1,2,3,4-tetrahydroquinoxalin-5-ylmethyl)-α-amino-(3-nitrobenzyl)phosphonic acid;

N-(2,3-dioxo-7-nitro-1,2,3,4-tetrahydroquinoxalin-5-ylmethyl)-α-amino-(2-hydroxy-3-methoxybenzyl) phosphonic acid;

N-(7-chloro-2,3-dioxo-1,2,3,4-tetrahydroquinoxalin-5-ylmethyl)-2-aminophenylphosphonic acid;

N-(2,3-dioxo-7-nitro-1,2,3,4-tetrahydroquinoxalin-5-ylmethyl)-α-amino-2-pyrrolylmethylphosphonic acid N-(2,3-dioxo-7-nitro-1,2,3,4-tetrahydroquinoxalin-5-ylmethyl)-α-amino-(3-methylsulfanylpropyl)phosphonic acid;

N-(2,3-dioxo-7-nitro-1,2,3,4-tetrahydroquinoxalin-5-ylmethyl)-amino-(2-hydroxy-2-methylpropyl)phosphonic acid;

N-(7-nitro-2,3-dioxo-1,2,3,4-tetrahydroquinoxalin-5-ylmethyl)-2-aminophenylphosphonic acid;

N-(7-chloro-2,3-dioxo-1,2,3,4-tetrahydroquinoxalin-5-ylmethyl)-α-aminoethylphosphonic acid;

N-(7-fluoro-2,3-dioxo-1,2,3,4-tetrahydroquinoxalin-5-ylmethyl)-(α-aminoethylphosphonic acid;

P-benzyl-N-(2,3-dioxo-7-nitro-1,2,3,4-tetrahydroquinoxalin-5-ylmethyl)aminomethylphosphinic acid;

P-methyl-N-(2,3-dioxo-7-nitro-1,2,3,4-tetrahydroquinoxalin-5-ylmethyl)-α-aminoethylphosphinic acid;

P-benzyl-(7-nitro-2,3-dioxo-1,2,3,4-tetrahydroquinoxalin-5-yl)aminomethanephosphinic acid;

P-methyl-(7-nitro-2,3-dioxo-1,2,3,4-tetrahydroquinoxalin-5-yl)aminomethanephosphinic acid;

N-(7-nitro-2,3-dioxo-1,2,3,4-tetrahydroquinoxalin-5-ylmethyl)-4-phosphonobutyramide;

N-(7-nitro-2,3-dioxo-1,2,3,4-tetrahydroquinoxalin-5-ylmethyl)-2-phosphonoacetamide;

N-(7-nitro-2,3-dioxo-1,2,3,4-tetrahydroquinoxalin-5-ylmethyl)-3-phosphonopropenoic acid amide;

N-(7-nitro-2,3-dioxo-1,2,3,4-tetrahydroquinoxalin-5-ylmethyl)-2-phosphonoindan-2-carboxamide;

N-benzyl-N-(2,3-dioxo-7-nitro-1,2,3,4-tetrahydroquinoxalin-5-yl)aminomethylphosphonic acid;

N-benzyl-N-(7-bromo-2,3-dioxo-1,2,3,4-tetrahydroquinoxalin-5-yl)aminomethylphosphonic acid;

N-benzyl-N-(7-chloro-2,3-dioxo-1,2,3,4-tetrahydroquinoxalin-5-yl)aminomethylphosphonic acid;

N-benzyl-N-(2,3-dioxo-7-fluoro-1,2,3,4-tetrahydroquinoxalin-5-yl)aminomethylphosphonic acid;

N-benzyl-N-(2,3-dioxo-7-nitro-1,2,3,4-tetrahydroquinoxalin-5-ylmethyl)-α-aminoethanephosphonic acid;

N-(2,3-dioxo-7-fluoro-1,2,3,4-tetrahydroquinoxalin-5-ylmethyl)-α-aminoethylphosphonic acid; (R)-N-(7-nitro-2,3-dioxo-1,2,3,4-tetrahydroquinoxalin-5-ylmethyl)-β-aminopropylphosphonic acid;

(S)-N-(7-nitro-2,3-dioxo-1,2,3,4-tetrahydroquinoxalin-5-ylmethyl)-β-aminopropylphosphonic acid;

N-(2,3-dioxo-7-nitro-1,2,3,4-tetrahydroquinoxalin-5-ylmethyl)-α-aminopropylphosphonic acid;

N-(2,3-dioxo-7-nitro-1,2,3,4-tetrahydroquinoxalin-5-ylmethyl)-α-amino(tetrahydropyran-4-yl)phosphonic acid;

N-(2,3-dioxo-7-nitro-1,2,3,4-tetrahydroquinoxalin-5-ylmethyl)-α-amino(piperidin-4-yl)phosphonic acid;

N-(2,3-dioxo-7-nitro-1,2,3,4-tetrahydroquinoxalin-5-ylmethyl)-α-amino(furan-2-ylmethyl)phosphonic acid;

N-(2,3-dioxo-7-nitro-1,2,3,4-tetrahydroquinoxalin-5-ylmethyl)-α-amino-(2-methoxy)ethylphosphonic acid;

N-(2,3-dioxo-7-nitro-1,2,3,4-tetrahydroquinoxalin-5-ylmethyl)-2-amino-2-cyclohexylethylphosphonic acid;

N-(2,3-dioxo-7-nitro-1,2,3,4-tetrahydroquinoxalin-5-ylmethyl)-β-aminoisopropylphosphonic acid;

N-(2,3-dioxo-7-nitro-1,2,3,4-tetrahydroquinoxalin-5-ylmethyl)-2-aminocyclohexylphosphonic acid;

N-(2,3-dioxo-7-nitro-1,2,3,4-tetrahydroquinoxalin-5-ylmethyl)-2-amino-2-methylpropylphosphonic acid;

N-(2,3-dioxo-7-nitro-1,2,3,4-tetrahydroquinoxalin-5-ylmethyl)-2-aminobutylphosphonic acid;

N-(2,3-dioxo-7-nitro-1,2,3,4-tetrahydroquinoxalin-5-ylmethyl)-2-aminoheptylphosphonic acid;

N-(2,3-dioxo-7-nitro-1,2,3,4-tetrahydroquinoxalin-5-ylmethyl)-2-amino-3-phenoxypropylphosphonic acid;

N-(2,3-dioxo-7-nitro-1,2,3,4-tetrahydroquinoxalin-5-ylmethyl)-2-ethylaminoethylphosphonic acid;

N-(2,3-dioxo-7-nitro-1,2,3,4-tetrahydroquinoxalin-5-ylmethyl)-2-benzylaminoethylphosphonic acid;

N-(2,3-dioxo-7-nitro-1,2,3,4-tetrahydroquinoxalin-5-ylmethyl)-2-amino-2-p-tolylethylphosphonic acid;

N-(2,3-dioxo-7-nitro-1,2,3,4-tetrahydroquinoxalin-5-ylmethyl)-2-amino-(2-methoxyphenyl)ethylphosphonic acid;

N-(2,3-dioxo-7-nitro-1,2,3,4-tetrahydroquinoxalin-5-ylmethyl)-2-amino-2-(4-fluorophenyl)ethylphosphonic acid;

N-(2,3-dioxo-7-nitro-1,2,3,4-tetrahydroquinoxalin-5-ylmethyl)-2-amino-2-phenylethylphosphonic acid;

P-methyl-N-(2,3-dioxo-7-nitro-1,2,3,4-tetrahydroquinoxalin-5-ylmethyl)-2-amino-2-phenylethylphosphinic acid;

N-(2,3-dioxo-7-nitro-1,2,3,4-tetrahydroquinoxalin-5-ylmethyl)-2-amino-1-phenylethylphosphonic acid;

N-(2,3-dioxo-7-nitro-1,2,3,4-tetrahydroquinoxalin-5-ylmethyl)-2-amino-1-(furan-2-yl)ethylphosphonic acid;

N-(2,3-dioxo-7-nitro-1,2,3,4-tetrahydroquinoxalin-5-ylmethyl)-2-amino-1-(4-fluorophenyl)ethylphosphonic acid;

N-(2,3-dioxo-7-nitro-1,2,3,4-tetrahydroquinoxalin-5-ylmethyl)-2-amino-1-(4-methoxyphenyl)ethylphosphonic acid;

N-(2,3-dioxo-7-nitro-1,2,3,4-tetrahydroquinoxalin-5-ylmethyl)-2-amino-1-(3-methoxyphenyl)ethylphosphonic acid;

N-(2,3-dioxo-7-nitro-1,2,3,4-tetrahydroquinoxalin-5-ylmethyl)-2-amino-1-(2-chlorophenyl)ethylphosphonic acid;

N-(2,3-dioxo-7-nitro-1,2,3,4-tetrahydroquinoxalin-5-ylmethyl)-2-amino-1-(4-tolyl)ethylphosphonic acid;

{1-[(7-bromo-2,3-dioxo-1,2,3,4-tetrahydroquinoxalin-5-ylmethyl)amino]cyclopropyl}-phosphonic acid;

N-benzyl-N-(7-bromo-2,3-dioxo-1,2,3,4-tetrahydroquinoxalin-5-ylmethyl)-α-aminoethylphosphonic acid;

N-benzyl-N-(7-chloro-2,3-dioxo-1,2,3,4-tetrahydroquinoxalin-5-ylmethyl)-α-aminoethylphosphonic acid and N-benzyl-N-(2,3-dioxo-7-fluoro-1,2,3,4-tetrahydroquinoxalin-5-ylmethyl)-α-aminoethylphosphonic acid;

N-(7-cyano-2,3-dioxo-1,2,3,4-tetrahydroquinoxalin-5-ylmethyl)-α-aminoethylphosphonic acid;

N-(7-cyano-2,3-dioxo-1,2,3,4-tetrahydroquinoxalin-5-ylmethyl)-α-ethylaminoethylphosphonic acid;

(R)-N-(7-trifluoromethyl-2,3-dioxo-1,2,3,4-tetrahydroquinoxalin-5-ylmethyl)-α-aminoethylphosphonic acid;

(S)-N-(7-trifluoromethyl-2,3-dioxo-1,2,3,4-tetrahydroquinoxalin-5-ylmethyl)-α-aminoethylphosphonic acid; and (R)-N-(7-trifluoromethyl-2,3-dioxo-1,2,3,4-tetrahydroquinoxalin-5-ylmethyl)-α-(ethylamino)ethylphosphonic acid;

N-(7-trifluoromethyl-2,3-dioxo-1,2,3,4-tetrahydroquinoxalin-5-ylmethyl)-β-(ethylamino)ethylphosphonic acid;

(S)-N-(7-trifluoromethyl-2,3-dioxo-1,2,3,4-tetrahydroquinoxalin-5-ylmethyl)-α-(ethylamino)ethylphosphonic acid;

(R)-N-(7-trifluoromethyl-2,3-dioxo-1,2,3,4-tetrahydroquinoxalin-5-ylmethyl)-β-aminopropylphosphonic acid;
(S)-N-(7-trifluoromethyl-2,3-dioxo-1,2,3,4-tetrahydroquinoxalin-5-ylmethyl)-β-aminopropylphosphonic acid;
N-(7-trifluoromethyl-2,3-dioxo-1,2,3,4-tetrahydroquinoxalin-5-ylmethyl)aminomethylphosphonic acid,
or a salt thereof.

7. A process for the preparation of compounds of the formula I

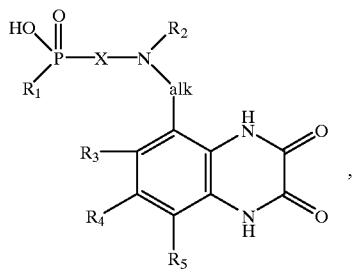

(I)

in which
  $R_1$ is hydroxyl or an aliphatic, araliphatic or aromatic radical,
  X is a divalent aliphatic, cycloaliphatic, cycloaliphatic-aliphatic, araliphatic, heteroarylaliphatic or aromatic radical,
  $R_2$ is hydrogen or an aliphatic or araliphatic radical, alk is lower alkylidene and
  $R_3$, $R_4$ and $R_5$ independently of one another are hydrogen, lower alkyl, halogen, trifluoromethyl, cyano or nitro, with the proviso that
    a1) $R_4$ is other than nitro when X is methylene, 3-hydroxybenzylidene, 3-methoxybenzylidene, 3-pyridylmethylene, ethylene, oxoethylene, ethylidene, 1,3-propylene, 1,3-(1-carboxy) propylene, cyclopropylene or 1,4-butylene, $R_1$ is hydroxyl, alk is methylene and $R_2$, $R_3$ and $R_5$ are hydrogen, or when X is methylene, $R_1$ is methyl or benzyl, alk is methylene and $R_2$, $R_3$ and $R_5$ are hydrogen, or when X is butylene, $R_1$ is hydroxyl, alk is methylene, $R_2$ is methyl and $R_3$ and $R_5$ are hydrogen and
    b1) $R_4$ is other than bromine when X is methylene or ethylidene, $R_1$ is hydroxyl, alk is methylene and $R_2$, $R_3$ and $R_5$ are hydrogen, and their salts, which comprises detaching, from a compound of the formula II

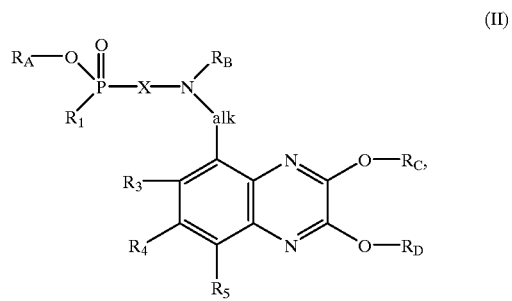

(II)

in which
  $R_A$ is hydrogen or a hydroxy protective group, $R_B$ is a group $R_2$ or an amino protective group and the radicals $R_C$ and $R_D$ are identical or different hydroxy protective groups and $R_1$, X, $R_2$, alk, $R_3$, $R_4$ and $R_5$ are as defined, the hydroxy protective groups $R_C$ and $R_D$ and a hydroxy protective group $R_A$ which may be present and an amino protective group $R_B$ which may be present and, if desired, in each case converting a compound obtained into another compound of the formula I, separating an isomer mixture obtainable according to the process into the components and separating off the preferred isomer in each case and/or converting a free compound obtainable according to the process into a salt or a salt obtainable according to the process into the corresponding free compound.

8. A pharmaceutical composition comprising a pharmaceutically acceptable carrier or diluent and a therapeutically effective amount of a compound according to claim 1, or a pharmaceutically acceptable salt thereof.

9. A method of treating pathological conditions which respond to blockage of excitatory amino acid receptors comprising administering to a subject in need of such treatment a therapeutically effective amount of a compound according to claim 1, or a pharmaceutically acceptable salt thereof.

* * * * *